United States Patent
Hoff et al.

(10) Patent No.: US 10,174,301 B2
(45) Date of Patent: Jan. 8, 2019

(54) METHODS FOR IMPROVING THE NUTRITIONAL VALUE OF THE ANIMAL FEED USING A PROTEASE

(71) Applicant: Novozymes A/S, Bagsvaerd (DK)

(72) Inventors: Tine Hoff, Holte (DK); Carsten Sjoeholm, Virum (DK); Peter Rahbek Oestergaard, Virum (DK); Katrine Pontoppidan, Lynge (DK)

(73) Assignee: Novozymes A/S, Bagsvaerd (DK)

( * ) Notice: Subject to any disclaimer, the term of this patent is extended or adjusted under 35 U.S.C. 154(b) by 876 days.

(21) Appl. No.: 14/363,933

(22) PCT Filed: Dec. 20, 2012

(86) PCT No.: PCT/EP2012/076355
§ 371 (c)(1),
(2) Date: Jun. 9, 2014

(87) PCT Pub. No.: WO2013/098185
PCT Pub. Date: Jul. 4, 2013

(65) Prior Publication Data
US 2015/0026843 A1  Jan. 22, 2015

Related U.S. Application Data

(60) Provisional application No. 61/581,684, filed on Dec. 30, 2011.

(30) Foreign Application Priority Data

Dec. 28, 2011 (EP) .................................. 11195932

(51) Int. Cl.
| | |
|---|---|
| A23K 50/00 | (2016.01) |
| C12N 9/54 | (2006.01) |
| C11D 3/386 | (2006.01) |
| A23K 20/189 | (2016.01) |
| A23K 50/75 | (2016.01) |
| A23K 50/30 | (2016.01) |
| A23K 50/60 | (2016.01) |

(52) U.S. Cl.
CPC .............. *C12N 9/54* (2013.01); *A23K 20/189* (2016.05); *A23K 50/30* (2016.05); *A23K 50/60* (2016.05); *A23K 50/75* (2016.05); *C11D 3/386* (2013.01)

(58) Field of Classification Search
None
See application file for complete search history.

(56) References Cited

U.S. PATENT DOCUMENTS

| | | | | |
|---|---|---|---|---|
| 6,107,455 A | * | 8/2000 | Rosholm | C08C 1/04 435/209 |
| 2010/0304433 A1 | * | 12/2010 | Udagawa | C12N 9/62 435/69.1 |

FOREIGN PATENT DOCUMENTS

| | | |
|---|---|---|
| WO | 95/28850 A1 | 11/1995 |
| WO | 96/05739 A2 | 2/1996 |
| WO | 01/58275 A2 | 8/2001 |
| WO | 2001/058276 A2 | 8/2001 |
| WO | 2004/034776 A2 | 4/2004 |
| WO | 2004/072221 A2 | 8/2004 |
| WO | 2004/072279 A2 | 8/2004 |
| WO | 2004/077960 A1 | 9/2004 |
| WO | 2004/111220 A1 | 12/2004 |
| WO | 2004/111221 A1 | 12/2004 |
| WO | 2004/111223 A1 | 12/2004 |
| WO | 2005/035747 A1 | 4/2005 |
| WO | 2005/066339 A2 | 7/2005 |
| WO | 2005/123911 A2 | 12/2005 |

OTHER PUBLICATIONS

Strauss et al, 1993 Hybridization With Radioactive Probes. In: Current Protocols in Molecular Biology (copyright 2000) John Wiley & Sons, Inc. Section 6.3.2.*
Strauss et al, 1993 Hybridization With Radioactive Probes. In: Current Protocols in Molecular Biology (copyright 2000) John Wiley & Sons, Inc. Section 6.3.1-6.3.6.*
Bao et al., UniProt Accession No. F7ZTR3 (2011).
Hu et al., UniProt Accession No. F0K735 (2011).
Hu et al., BMC Genomics, vol. 12, No. 93, pp. 1-18 (2011).
Nolling et al., UniProt Accession No. Q97LD7 (2001).
Nolliing et al., Journal of Bacteriology, vol. 183, No. 16, pp. 4823-4838 (2001).
Rawlings et al., Biochimie, vol. 90, pp. 243-259 (2008).
Siezen et al., Proteins: Structure, Function and Bioinformatics, vol. 67, pp. 681-694 (2007).
Wlodawer et al., Acta Biochimica Polonica, vol. 50, No. 1, pp. 81-102 (2003).

* cited by examiner

*Primary Examiner* — Sheridan Swope
(74) *Attorney, Agent, or Firm* — Elias Lambiris

(57) ABSTRACT

The present invention relates to isolated polypeptides having protease activity and isolated polynucleotides encoding the polypeptides. The invention also relates to nucleic acid constructs, vectors, and host cells comprising the polynucleotides as well as methods of producing and using the polypeptides in e.g. animal feed and detergents.

17 Claims, 4 Drawing Sheets
Specification includes a Sequence Listing.

SEQUENCE LISTING

<160> NUMBER OF SEQ ID NOS: 11

<210> SEQ ID NO 1
<211> LENGTH: 1920
<212> TYPE: DNA
<213> ORGANISM: Bacillus sp. 19138
<220> FEATURE:
<221> NAME/KEY: CDS
<222> LOCATION: (1)..(1917)
<220> FEATURE:
<221> NAME/KEY: sig_peptide
<222> LOCATION: (1)..(84)
<220> FEATURE:
<221> NAME/KEY: mat_peptide
<222> LOCATION: (613)..(1917)

<400> SEQUENCE: 1

```
atg aaa aaa tta agt aaa aaa ttg ctt gcc gta gct gcg gca ggt         45
Met Lys Lys Leu Ser Lys Lys Leu Leu Ala Val Ala Ala Ala Gly
            -200             -195                 -190 acg ctg ttg ctt gca acc gtg cca agc att gcc ttt gca gac act         90
Thr Leu Leu Leu Ala Thr Val Pro Ser Ile Ala Phe Ala Asp Thr
            -185             -180                 -175 gcg caa gaa atc ccc caa ggc gta ggt tcc ggt gtg ctg tcc aac        135
Ala Gln Glu Ile Pro Gln Gly Val Gly Ser Gly Val Leu Ser Asn
            -170             -165                 -160 gtc gac tat ttc ggt ggt ctc gat cca agc act gtg gta acg gtt        180
Val Asp Tyr Phe Gly Gly Leu Asp Pro Ser Thr Val Val Thr Val
            -155             -150                 -145 gat atc gtc atg aaa atc caa aac aaa tac gac ttg gcc aac tac        225
Asp Ile Val Met Lys Ile Gln Asn Lys Tyr Asp Leu Ala Asn Tyr
            -140             -135                 -130 atc aag gaa acg acc tct ccg ggt agc aac acc tac cat aaa tac        270
Ile Lys Glu Thr Thr Ser Pro Gly Ser Asn Thr Tyr His Lys Tyr
            -125             -120                 -115 ctg aca ccg acg caa ttc aaa gcc aaa tac gca cct tct cca gcg        315
Leu Thr Pro Thr Gln Phe Lys Ala Lys Tyr Ala Pro Ser Pro Ala
            -110             -105                 -100 agc gtc aat gcg att act cac tat ctc tcg tcc tat ggc atc acg tct    363
Ser Val Asn Ala Ile Thr His Tyr Leu Ser Ser Tyr Gly Ile Thr Ser
            -95              -90                  -85 tcc gtt tac ccg gac aac ctg atc atc aca gcg acc ggc acc gtc ggt    411
Ser Val Tyr Pro Asp Asn Leu Ile Ile Thr Ala Thr Gly Thr Val Gly
            -80              -75                  -70 caa ttc aac aac gcg ttc aac gtc acc att gaa cgt gcc caa tac aaa    459
Gln Phe Asn Asn Ala Phe Asn Val Thr Ile Glu Arg Ala Gln Tyr Lys
        -65              -60                  -55 ggc aag agc ttc cat gca tcc aaa acc aac cct aaa gca ccg gct gcc    507
Gly Lys Ser Phe His Ala Ser Lys Thr Asn Pro Lys Ala Pro Ala Ala
    -50                  -45                  -40 atc gcc gac tcc atc ctg tgc att ttg ggc atc agc aac tac tcc aac    555
Ile Ala Asp Ser Ile Leu Cys Ile Leu Gly Ile Ser Asn Tyr Ser Asn
```

```
        -35                -30                -25                -20
ttc act tcg cac att gcg aaa cag cag ccg ctc gac agc agc caa tcc    603
Phe Thr Ser His Ile Ala Lys Gln Gln Pro Leu Asp Ser Ser Gln Ser
                -15                -10                 -5 aca gcg aac gtc acg ccg aac ccg acc ggc cgc atg acc aac gac ttg    651
Thr Ala Asn Val Thr Pro Asn Pro Thr Gly Arg Met Thr Asn Asp Leu
         -1  1                  5                  10 gtg tcc cgt tac aac gta caa ccc ttg tac acc aaa gga gcc aac ggt    699
Val Ser Arg Tyr Asn Val Gln Pro Leu Tyr Thr Lys Gly Ala Asn Gly
         15                  20                 25 tcc ggt caa acg atc ggc atc gtg acg ctg gct gat ttc aac ccg agt    747
Ser Gly Gln Thr Ile Gly Ile Val Thr Leu Ala Asp Phe Asn Pro Ser
 30                  35                 40                 45 gat gcc tac tcg tac tgg cag tac aac aac atc aac gtc aac ccg aac    795
Asp Ala Tyr Ser Tyr Trp Gln Tyr Asn Asn Ile Asn Val Asn Pro Asn
                 50                  55                 60 cgc atc acc aaa atc aac gtg gac ggt ggt tcc ggc ctg agt gaa gat    843
Arg Ile Thr Lys Ile Asn Val Asp Gly Gly Ser Gly Leu Ser Glu Asp
             65                  70                 75 gcc ggt tca gac gaa aca tcg ctc gac gtg gaa caa tcc gga gct ctg    891
Ala Gly Ser Asp Glu Thr Ser Leu Asp Val Glu Gln Ser Gly Ala Leu
         80                  85                 90 gca ccg ggc gca aac ctc aat gtc tat gtc ggc ccg aac acc gat aca    939
Ala Pro Gly Ala Asn Leu Asn Val Tyr Val Gly Pro Asn Thr Asp Thr
     95                 100                 105 ggg ttt gtg gat gcg tac gca aaa gcg atc aac gac aac gtc gca cac    987
Gly Phe Val Asp Ala Tyr Ala Lys Ala Ile Asn Asp Asn Val Ala His
110                 115                 120                 125 cag atc tcc gca agc tgg ggc gaa tcc gaa tcg ctg att aat tac tac   1035
Gln Ile Ser Ala Ser Trp Gly Glu Ser Glu Ser Leu Ile Asn Tyr Tyr
                130                 135                 140 gtc caa cag caa atg gaa aca cct gag tat gcg gaa aca ttc aac caa   1083
Val Gln Gln Gln Met Glu Thr Pro Glu Tyr Ala Glu Thr Phe Asn Gln
            145                 150                 155 ctc ttc atg caa gca gcg gca cag gga act tcg atg ttc gcg tcg gct   1131
Leu Phe Met Gln Ala Ala Ala Gln Gly Thr Ser Met Phe Ala Ser Ala
                160                 165                 170 ggt gac tcc ggt gcc tat gat gct tcc ggt gac ctc aac acg tac gat   1179
Gly Asp Ser Gly Ala Tyr Asp Ala Ser Gly Asp Leu Asn Thr Tyr Asp
        175                 180                 185 ctc tcc gtc gac aat ccg gct gac agc ccg tac atc acg gcg gcc ggc   1227
Leu Ser Val Asp Asn Pro Ala Asp Ser Pro Tyr Ile Thr Ala Ala Gly
190                 195                 200                 205 ggc acc acc gtg ccg ttt acc tat acg tcg acg caa tac aac ctg tcg   1275
Gly Thr Thr Val Pro Phe Thr Tyr Thr Ser Thr Gln Tyr Asn Leu Ser
                210                 215                 220 att acc gta ccg caa gaa cgc gca tgg ggc tgg gat tat ctc tac ccg   1323
Ile Thr Val Pro Gln Glu Arg Ala Trp Gly Trp Asp Tyr Leu Tyr Pro
            225                 230                 235 ctg ttt gac gca cgc ggc ttg aac aac ccg acc ggc tgg gca caa cgt   1371
Leu Phe Asp Ala Arg Gly Leu Asn Asn Pro Thr Gly Trp Ala Gln Arg
                240                 245                 250 tac ttt gtc ggc ggc ggc ggt ttc agc caa ctc ttc gca aca cct   1419
Tyr Phe Val Gly Gly Gly Gly Phe Ser Gln Leu Phe Ala Thr Pro
        255                 260                 265 gac tac caa acc ggc gta tcc ggc gtg aac agc tac acc gct gtc cac   1467
Asp Tyr Gln Thr Gly Val Ser Gly Val Asn Ser Tyr Thr Ala Val His
270                 275                 280                 285 caa tgg act ccg agt tcc gac ttc acc tcg gtc act cgt gac gca caa   1515
```

```
Gln Trp Thr Pro Ser Ser Asp Phe Thr Ser Val Thr Arg Asp Ala Gln
            290                 295                 300 ccg acc atc gtc acc ggc aca ggc acc ggc cgt aac ctg cct gac ctg      1563
Pro Thr Ile Val Thr Gly Thr Gly Thr Gly Arg Asn Leu Pro Asp Leu
            305                 310                 315 tcg atg aac gcc gac ccg tac acc ggc tac tcc gtg tac ttc aac ttg      1611
Ser Met Asn Ala Asp Pro Tyr Thr Gly Tyr Ser Val Tyr Phe Asn Leu
            320                 325                 330 ccg acc acg aac ggt gcg acg aca gta gac tcc ggc tgg gca acg tac      1659
Pro Thr Thr Asn Gly Ala Thr Thr Val Asp Ser Gly Trp Ala Thr Tyr
            335                 340                 345 ggc ggt act tcc ttt gta gca ccg caa ttg gca ggt ctc agc gcg ttg      1707
Gly Gly Thr Ser Phe Val Ala Pro Gln Leu Ala Gly Leu Ser Ala Leu
350                 355                 360                 365 atc aac agt gca aac ggc agc gaa gca ggc ttc tgg aac cct cag ctc      1755
Ile Asn Ser Ala Asn Gly Ser Glu Ala Gly Phe Trp Asn Pro Gln Leu
                370                 375                 380 tac cgt ttt gca caa agc aat cac tcg ccg ttg cac ccg ctc aac acc      1803
Tyr Arg Phe Ala Gln Ser Asn His Ser Pro Leu His Pro Leu Asn Thr
            385                 390                 395 gca ggc gca tcc aac gac aac gtc ttc tat tcc ggc act ccg ggc gcc      1851
Ala Gly Ala Ser Asn Asp Asn Val Phe Tyr Ser Gly Thr Pro Gly Ala
            400                 405                 410 atc tac aac caa gca acc ggt ctt ggc acg ccc gac gtg acg gca ctt      1899
Ile Tyr Asn Gln Ala Thr Gly Leu Gly Thr Pro Asp Val Thr Ala Leu
            415                 420                 425 gca caa gcg ttt ggc aaa taa                                          1920
Ala Gln Ala Phe Gly Lys
430                 435

<210> SEQ ID NO 2
<211> LENGTH: 639
<212> TYPE: PRT
<213> ORGANISM: Bacillus sp. 19138

<400> SEQUENCE: 2

Met Lys Lys Leu Ser Lys Lys Leu Leu Ala Val Ala Ala Ala Gly
                -200                -195                -190

Thr Leu Leu Leu Ala  Thr Val Pro Ser Ile  Ala Phe Ala Asp Thr
                -185                -180                -175

Ala Gln Glu Ile Pro  Gln Gly Val Gly Ser  Gly Val Leu Ser Asn
                -170                -165                -160

Val Asp Tyr Phe Gly  Gly Leu Asp Pro Ser  Thr Val Val Thr Val
                -155                -150                -145

Asp Ile Val Met Lys  Ile Gln Asn Lys Tyr  Asp Leu Ala Asn Tyr
                -140                -135                -130

Ile Lys Glu Thr Thr  Ser Pro Gly Ser Asn  Thr Tyr His Lys Tyr
                -125                -120                -115

Leu Thr Pro Thr Gln  Phe Lys Ala Lys Tyr  Ala Pro Ser Pro Ala
                -110                -105                -100

Ser Val Asn Ala Ile  Thr His Tyr Leu Ser  Ser Tyr Gly Ile Thr Ser
                -95                 -90                 -85

Ser Val Tyr Pro Asp  Asn Leu Ile Ile Thr  Ala Thr Gly Thr Val Gly
                -80                 -75                 -70

Gln Phe Asn Asn Ala  Phe Asn Val Thr Ile  Glu Arg Ala Gln Tyr Lys
                -65                 -60                 -55

Gly Lys Ser Phe His  Ala Ser Leu Thr Asn  Pro Lys Ala Pro Ala Ala
                -50                 -45                 -40
```

```
Ile Ala Asp Ser Ile Leu Cys Ile Leu Gly Ile Ser Asn Tyr Ser Asn
-35              -30              -25              -20

Phe Thr Ser His Ile Ala Lys Gln Gln Pro Leu Asp Ser Ser Gln Ser
            -15              -10               -5

Thr Ala Asn Val Thr Pro Asn Pro Thr Gly Arg Met Thr Asn Asp Leu
         -1   1            5                    10

Val Ser Arg Tyr Asn Val Gln Pro Leu Tyr Thr Lys Gly Ala Asn Gly
     15              20              25

Ser Gly Gln Thr Ile Gly Ile Val Thr Leu Ala Asp Phe Asn Pro Ser
 30              35              40              45

Asp Ala Tyr Ser Tyr Trp Gln Tyr Asn Asn Ile Asn Val Asn Pro Asn
             50              55              60

Arg Ile Thr Lys Ile Asn Val Asp Gly Gly Ser Gly Leu Ser Glu Asp
             65              70              75

Ala Gly Ser Asp Glu Thr Ser Leu Asp Val Glu Gln Ser Gly Ala Leu
         80              85              90

Ala Pro Gly Ala Asn Leu Asn Val Tyr Val Gly Pro Asn Thr Asp Thr
     95             100             105

Gly Phe Val Asp Ala Tyr Ala Lys Ala Ile Asn Asp Asn Val Ala His
110             115             120             125

Gln Ile Ser Ala Ser Trp Gly Glu Ser Glu Ser Leu Ile Asn Tyr Tyr
            130             135             140

Val Gln Gln Gln Met Glu Thr Pro Glu Tyr Ala Glu Thr Phe Asn Gln
            145             150             155

Leu Phe Met Gln Ala Ala Ala Gln Gly Thr Ser Met Phe Ala Ser Ala
            160             165             170

Gly Asp Ser Gly Ala Tyr Asp Ala Ser Gly Asp Leu Asn Thr Tyr Asp
        175             180             185

Leu Ser Val Asp Asn Pro Ala Asp Ser Pro Tyr Ile Thr Ala Ala Gly
190             195             200             205

Gly Thr Thr Val Pro Phe Thr Tyr Thr Ser Thr Gln Tyr Asn Leu Ser
            210             215             220

Ile Thr Val Pro Gln Glu Arg Ala Trp Gly Trp Asp Tyr Leu Tyr Pro
            225             230             235

Leu Phe Asp Ala Arg Gly Leu Asn Asn Pro Thr Gly Trp Ala Gln Arg
        240             245             250

Tyr Phe Val Gly Gly Gly Gly Phe Ser Gln Leu Phe Ala Thr Pro
        255             260             265

Asp Tyr Gln Thr Gly Val Ser Gly Val Asn Ser Tyr Thr Ala Val His
270             275             280             285

Gln Trp Thr Pro Ser Ser Asp Phe Thr Ser Val Thr Arg Asp Ala Gln
            290             295             300

Pro Thr Ile Val Thr Gly Thr Gly Thr Arg Asn Leu Pro Asp Leu
        305             310             315

Ser Met Asn Ala Asp Pro Tyr Thr Gly Tyr Ser Val Tyr Phe Asn Leu
            320             325             330

Pro Thr Thr Asn Gly Ala Thr Thr Val Asp Ser Gly Trp Ala Thr Tyr
        335             340             345

Gly Gly Thr Ser Phe Val Ala Pro Gln Leu Ala Gly Leu Ser Ala Leu
350             355             360             365

Ile Asn Ser Ala Asn Gly Ser Glu Ala Gly Phe Trp Asn Pro Gln Leu
            370             375             380
```

```
Tyr Arg Phe Ala Gln Ser Asn His Ser Pro Leu His Pro Leu Asn Thr
            385                 390                 395

Ala Gly Ala Ser Asn Asp Asn Val Phe Tyr Ser Gly Thr Pro Gly Ala
        400                 405                 410

Ile Tyr Asn Gln Ala Thr Gly Leu Gly Thr Pro Asp Val Thr Ala Leu
        415                 420                 425

Ala Gln Ala Phe Gly Lys
430             435

<210> SEQ ID NO 3
<211> LENGTH: 1935
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(1935)
<220> FEATURE:
<221> NAME/KEY: sig_peptide
<222> LOCATION: (1)..(81)
<220> FEATURE:
<221> NAME/KEY: mat_peptide
<222> LOCATION: (610)..(1929)

<400> SEQUENCE: 3 atg aag aaa ccg ttg ggg aaa att gtc gca agc acc gca cta ctc         45
Met Lys Lys Pro Leu Gly Lys Ile Val Ala Ser Thr Ala Leu Leu
        -200                -195                -190 att tct gtt gct ttt agt tca tcg atc gca tcg gct gac act gcg         90
Ile Ser Val Ala Phe Ser Ser Ser Ile Ala Ser Ala Asp Thr Ala
        -185                -180                -175 caa gaa atc ccc caa ggc gta ggt tcc ggt gtg ctg tcc aac gtc        135
Gln Glu Ile Pro Gln Gly Val Gly Ser Gly Val Leu Ser Asn Val
        -170                -165                -160 gac tat ttc ggt ggt ctc gat cca agc act gtg gta acg gtt gat        180
Asp Tyr Phe Gly Gly Leu Asp Pro Ser Thr Val Val Thr Val Asp
        -155                -150                -145 atc gtc atg aaa atc caa aac aaa tac gac ttg gcc aac tac atc        225
Ile Val Met Lys Ile Gln Asn Lys Tyr Asp Leu Ala Asn Tyr Ile
        -140                -135                -130 aag gaa acg acc tct ccg ggt agc aac acc tac cat aaa tac ctg        270
Lys Glu Thr Thr Ser Pro Gly Ser Asn Thr Tyr His Lys Tyr Leu
        -125                -120                -115 aca ccg acg caa ttc aaa gcc aaa tac gca cct tct cca gcg agc        315
Thr Pro Thr Gln Phe Lys Ala Lys Tyr Ala Pro Ser Pro Ala Ser
        -110                -105                -100 gtc aat gcg att act cac tat ctc tcg tcc tat ggc atc acg tct tcc   363
Val Asn Ala Ile Thr His Tyr Leu Ser Ser Tyr Gly Ile Thr Ser Ser
            -95                 -90                 -85 gtt tac ccg gac aac ctg atc atc aca gcg acc ggc acc gtc ggt caa   411
Val Tyr Pro Asp Asn Leu Ile Ile Thr Ala Thr Gly Thr Val Gly Gln
        -80                 -75                 -70 ttc aac aac gcg ttc aac gtc acc att gaa cgt gcc caa tac aaa ggc   459
Phe Asn Asn Ala Phe Asn Val Thr Ile Glu Arg Ala Gln Tyr Lys Gly
        -65                 -60                 -55 aag agc ttc cat gca tcc aaa acc aac cct aaa gca ccg gct gcc atc   507
Lys Ser Phe His Ala Ser Lys Thr Asn Pro Lys Ala Pro Ala Ala Ile
-50                 -45                 -40                 -35 gcc gac tcc atc ctg tgc att ttg ggc atc agc aac tac tcc aac ttc   555
Ala Asp Ser Ile Leu Cys Ile Leu Gly Ile Ser Asn Tyr Ser Asn Phe
            -30                 -25                 -20
```

| | | |
|---|---|---|
| act tcg cac att gcg aaa cag cag ccg ctc gac agc agc caa tcc aca<br>Thr Ser His Ile Ala Lys Gln Gln Pro Leu Asp Ser Ser Gln Ser Thr<br>          -15                          -10                       -5 | | 603 |
| gcg aac gtc acg ccg aac ccg acc ggc cgc atg acc aac gac ttg gtg<br>Ala Asn Val Thr Pro Asn Pro Thr Gly Arg Met Thr Asn Asp Leu Val<br>          -1  1                    5                         10 | | 651 |
| tcc cgt tac aac gta caa ccc ttg tac acc aaa gga gcc aac ggt tcc<br>Ser Arg Tyr Asn Val Gln Pro Leu Tyr Thr Lys Gly Ala Asn Gly Ser<br>15                   20                    25                  30 | | 699 |
| ggt caa acg atc ggc atc gtg acg ctg gct gat ttc aac ccg agt gat<br>Gly Gln Thr Ile Gly Ile Val Thr Leu Ala Asp Phe Asn Pro Ser Asp<br>                   35                    40                  45 | | 747 |
| gcc tac tcg tac tgg cag tac aac aac atc aac gtc aac ccg aac cgc<br>Ala Tyr Ser Tyr Trp Gln Tyr Asn Asn Ile Asn Val Asn Pro Asn Arg<br>           50                    55                    60 | | 795 |
| atc acc aaa atc aac gtg gac ggt ggt tcc ggc ctg agt gaa gat gcc<br>Ile Thr Lys Ile Asn Val Asp Gly Gly Ser Gly Leu Ser Glu Asp Ala<br>               65                    70                  75 | | 843 |
| ggt tca gac gaa aca tcg ctc gac gtg gaa caa tcc gga gct ctg gca<br>Gly Ser Asp Glu Thr Ser Leu Asp Val Glu Gln Ser Gly Ala Leu Ala<br>80                   85                    90 | | 891 |
| ccg ggc gca aac ctc aat gtc tat gtc ggc ccg aac acc gat aca ggg<br>Pro Gly Ala Asn Leu Asn Val Tyr Val Gly Pro Asn Thr Asp Thr Gly<br>95                 100               105               110 | | 939 |
| ttt gtg gat gcg tac gca aaa gcg atc aac gac aac gtc gca cac cag<br>Phe Val Asp Ala Tyr Ala Lys Ala Ile Asn Asp Asn Val Ala His Gln<br>                   115                  120               125 | | 987 |
| atc tcc gca agc tgg ggc gaa tcc gaa tcg ctg att aat tac tac gtc<br>Ile Ser Ala Ser Trp Gly Glu Ser Glu Ser Leu Ile Asn Tyr Tyr Val<br>              130                  135                  140 | | 1035 |
| caa cag caa atg gaa aca cct gag tat gcg gaa aca ttc aac caa ctc<br>Gln Gln Gln Met Glu Thr Pro Glu Tyr Ala Glu Thr Phe Asn Gln Leu<br>                   145                  150               155 | | 1083 |
| ttc atg caa gca gcg gca cag gga act tcg atg ttc gcg tcg gct ggt<br>Phe Met Gln Ala Ala Ala Gln Gly Thr Ser Met Phe Ala Ser Ala Gly<br>          160                  165                  170 | | 1131 |
| gac tcc ggt gcc tat gat gct tcc ggt gac ctc aac acg tac gat ctc<br>Asp Ser Gly Ala Tyr Asp Ala Ser Gly Asp Leu Asn Thr Tyr Asp Leu<br>175                   180                  185               190 | | 1179 |
| tcc gtc gac aat ccg gct gac agc ccg tac atc acg gcg gcc ggc ggc<br>Ser Val Asp Asn Pro Ala Asp Ser Pro Tyr Ile Thr Ala Ala Gly Gly<br>                   195                  200               205 | | 1227 |
| acc acc gtg ccg ttt acc tat acg tcg acg caa tac aac ctg tcg att<br>Thr Thr Val Pro Phe Thr Tyr Thr Ser Thr Gln Tyr Asn Leu Ser Ile<br>              210                  215                  220 | | 1275 |
| acc gta ccg caa gaa cgc gca tgg ggc tgg gat tat ctc tac ccg ctg<br>Thr Val Pro Gln Glu Arg Ala Trp Gly Trp Asp Tyr Leu Tyr Pro Leu<br>          225                  230                  235 | | 1323 |
| ttt gac gca cgc ggc ttg aac aac ccg acc ggc tgg gca caa cgt tac<br>Phe Asp Ala Arg Gly Leu Asn Asn Pro Thr Gly Trp Ala Gln Arg Tyr<br>240                   245                  250 | | 1371 |
| ttt gtc ggc ggc ggc ggc ggt ttc agc caa ctc ttc gca aca cct gac<br>Phe Val Gly Gly Gly Gly Gly Phe Ser Gln Leu Phe Ala Thr Pro Asp<br>255                 260               265               270 | | 1419 |
| tac caa acc ggc gta tcc ggc gtg aac agc tac acc gct gtc cac caa<br>Tyr Gln Thr Gly Val Ser Gly Val Asn Ser Tyr Thr Ala Val His Gln<br>                   275                  280               285 | | 1467 |
| tgg act ccg agt tcc gac ttc acc tcg gtc act cgt gac gca caa ccg<br>Trp Thr Pro Ser Ser Asp Phe Thr Ser Val Thr Arg Asp Ala Gln Pro<br>              290                  295                  300 | | 1515 |

```
acc atc gtc acc ggc aca ggc acc ggc cgt aac ctg cct gac ctg tcg    1563
Thr Ile Val Thr Gly Thr Gly Thr Gly Arg Asn Leu Pro Asp Leu Ser
        305                 310                 315 atg aac gcc gac ccg tac acc ggc tac tcc gtg tac ttc aac ttg ccg    1611
Met Asn Ala Asp Pro Tyr Thr Gly Tyr Ser Val Tyr Phe Asn Leu Pro
320                 325                 330 acc acg aac ggt gcg acg aca gta gac tcc ggc tgg gca acg tac ggc    1659
Thr Thr Asn Gly Ala Thr Thr Val Asp Ser Gly Trp Ala Thr Tyr Gly
335                 340                 345                 350 ggt act tcc ttt gta gca ccg caa ttg gca ggt ctc agc gcg ttg atc    1707
Gly Thr Ser Phe Val Ala Pro Gln Leu Ala Gly Leu Ser Ala Leu Ile
            355                 360                 365 aac agt gca aac ggc agc gaa gca ggc ttc tgg aac cct cag ctc tac    1755
Asn Ser Ala Asn Gly Ser Glu Ala Gly Phe Trp Asn Pro Gln Leu Tyr
        370                 375                 380 cgt ttt gca caa agc aat cac tcg ccg ttg cac ccg ctc aac acc gca    1803
Arg Phe Ala Gln Ser Asn His Ser Pro Leu His Pro Leu Asn Thr Ala
    385                 390                 395 ggc gca tcc aac gac aac gtc ttc tat tcc ggc act ccg ggc gcc atc    1851
Gly Ala Ser Asn Asp Asn Val Phe Tyr Ser Gly Thr Pro Gly Ala Ile
400                 405                 410 tac aac caa gca acc ggt ctt ggc acg ccc gac gtg acg gca ctt gca    1899
Tyr Asn Gln Ala Thr Gly Leu Gly Thr Pro Asp Val Thr Ala Leu Ala
415                 420                 425                 430 caa gcg ttt ggc aaa cat cag cac caa cac cag cat                    1935
Gln Ala Phe Gly Lys His Gln His Gln His Gln His
            435                 440

<210> SEQ ID NO 4
<211> LENGTH: 645
<212> TYPE: PRT
<213> ORGANISM: Artificial sequence
<220> FEATURE:
<223> OTHER INFORMATION: Synthetic Construct

<400> SEQUENCE: 4

Met Lys Lys Pro  Leu Gly Lys Ile  Val Ala Ser Thr  Ala Leu Leu
            -200                -195                -190

Ile Ser Val Ala  Phe Ser Ser Ser  Ile Ala Ser Ala  Asp Thr Ala
            -185                -180                -175

Gln Glu Ile Pro  Gln Gly Val Gly  Ser Gly Val Leu  Ser Asn Val
            -170                -165                -160

Asp Tyr Phe Gly  Gly Leu Asp Pro  Ser Thr Val Val  Thr Val Asp
            -155                -150                -145

Ile Val Met Lys  Ile Gln Asn Lys  Tyr Asp Leu Ala  Asn Tyr Ile
            -140                -135                -130

Lys Glu Thr Thr  Ser Pro Gly Ser  Asn Thr Tyr His  Lys Tyr Leu
            -125                -120                -115

Thr Pro Thr Gln  Phe Lys Ala Lys  Tyr Ala Pro Ser  Pro Ala Ser
            -110                -105                -100

Val Asn Ala Ile  Thr His Tyr Leu  Ser Ser Tyr Gly  Ile Thr Ser Ser
            -95                 -90                 -85

Val Tyr Pro Asp  Asn Leu Ile Ile  Thr Ala Thr Gly  Thr Val Gly Gln
            -80                 -75                 -70

Phe Asn Asn Ala  Phe Asn Val Thr  Ile Glu Arg Ala  Gln Tyr Lys Gly
            -65                 -60                 -55

Lys Ser Phe His  Ala Ser Lys Thr  Asn Pro Lys Ala  Pro Ala Ala Ile
-50                 -45                 -40                 -35
```

```
Ala Asp Ser Ile Leu Cys Ile Leu Gly Ile Ser Asn Tyr Ser Asn Phe
            -30                 -25                 -20

Thr Ser His Ile Ala Lys Gln Gln Pro Leu Asp Ser Ser Gln Ser Thr
            -15                 -10                  -5

Ala Asn Val Thr Pro Asn Pro Thr Gly Arg Met Thr Asn Asp Leu Val
         -1   1                  5                  10

Ser Arg Tyr Asn Val Gln Pro Leu Tyr Thr Lys Gly Ala Asn Gly Ser
 15                  20                  25                  30

Gly Gln Thr Ile Gly Ile Val Thr Leu Ala Asp Phe Asn Pro Ser Asp
                 35                  40                  45

Ala Tyr Ser Tyr Trp Gln Tyr Asn Asn Ile Asn Val Asn Pro Asn Arg
             50                  55                  60

Ile Thr Lys Ile Asn Val Asp Gly Gly Ser Gly Leu Ser Glu Asp Ala
                 65                  70                  75

Gly Ser Asp Glu Thr Ser Leu Asp Val Glu Gln Ser Gly Ala Leu Ala
 80                  85                  90

Pro Gly Ala Asn Leu Asn Val Tyr Val Gly Pro Asn Thr Asp Thr Gly
 95                 100                 105                 110

Phe Val Asp Ala Tyr Ala Lys Ala Ile Asn Asp Asn Val Ala His Gln
                115                 120                 125

Ile Ser Ala Ser Trp Gly Glu Ser Glu Ser Leu Ile Asn Tyr Tyr Val
            130                 135                 140

Gln Gln Gln Met Glu Thr Pro Glu Tyr Ala Glu Thr Phe Asn Gln Leu
            145                 150                 155

Phe Met Gln Ala Ala Gln Gly Thr Ser Met Phe Ala Ser Ala Gly
    160                 165                 170

Asp Ser Gly Ala Tyr Asp Ala Ser Gly Asp Leu Asn Thr Tyr Asp Leu
175                 180                 185                 190

Ser Val Asp Asn Pro Ala Asp Ser Pro Tyr Ile Thr Ala Ala Gly Gly
                195                 200                 205

Thr Thr Val Pro Phe Thr Tyr Thr Ser Thr Gln Tyr Asn Leu Ser Ile
                210                 215                 220

Thr Val Pro Gln Glu Arg Ala Trp Gly Trp Asp Tyr Leu Tyr Pro Leu
            225                 230                 235

Phe Asp Ala Arg Gly Leu Asn Asn Pro Thr Gly Trp Ala Gln Arg Tyr
240                 245                 250

Phe Val Gly Gly Gly Gly Gly Phe Ser Gln Leu Phe Ala Thr Pro Asp
255                 260                 265                 270

Tyr Gln Thr Gly Val Ser Gly Val Asn Ser Tyr Thr Ala Val His Gln
                275                 280                 285

Trp Thr Pro Ser Ser Asp Phe Thr Ser Val Thr Arg Asp Ala Gln Pro
            290                 295                 300

Thr Ile Val Thr Gly Thr Gly Thr Gly Arg Asn Leu Pro Asp Leu Ser
            305                 310                 315

Met Asn Ala Asp Pro Tyr Thr Gly Tyr Ser Val Tyr Phe Asn Leu Pro
            320                 325                 330

Thr Thr Asn Gly Ala Thr Thr Val Asp Ser Gly Trp Ala Thr Tyr Gly
335                 340                 345                 350

Gly Thr Ser Phe Val Ala Pro Gln Leu Ala Gly Leu Ser Ala Leu Ile
                355                 360                 365

Asn Ser Ala Asn Gly Ser Glu Ala Gly Phe Trp Asn Pro Gln Leu Tyr
            370                 375                 380
```

```
Arg Phe Ala Gln Ser Asn His Ser Pro Leu His Pro Leu Asn Thr Ala
            385                 390                 395

Gly Ala Ser Asn Asp Asn Val Phe Tyr Ser Gly Thr Pro Gly Ala Ile
400                 405                 410

Tyr Asn Gln Ala Thr Gly Leu Gly Thr Pro Asp Val Thr Ala Leu Ala
415                 420                 425                 430

Gln Ala Phe Gly Lys His Gln His Gln His Gln His
                435                 440

<210> SEQ ID NO 5
<211> LENGTH: 435
<212> TYPE: PRT
<213> ORGANISM: Bacillus sp.

<400> SEQUENCE: 5

Val Thr Pro Asn Pro Thr Gly Arg Met Thr Asn Asp Leu Val Ser Arg
1               5                   10                  15

Tyr Asn Val Gln Pro Leu Tyr Thr Lys Gly Ala Asn Gly Ser Gly Gln
            20                  25                  30

Thr Ile Gly Ile Val Thr Leu Ala Asp Phe Asn Pro Ser Asp Ala Tyr
        35                  40                  45

Ser Tyr Trp Gln Tyr Asn Asn Ile Asn Val Asn Pro Asn Arg Ile Thr
    50                  55                  60

Lys Ile Asn Val Asp Gly Gly Ser Gly Leu Ser Glu Asp Ala Gly Ser
65                  70                  75                  80

Asp Glu Thr Ser Leu Asp Val Glu Gln Ser Gly Ala Leu Ala Pro Gly
                85                  90                  95

Ala Asn Leu Asn Val Tyr Val Gly Pro Asn Thr Asp Thr Gly Phe Val
            100                 105                 110

Asp Ala Tyr Ala Lys Ala Ile Asn Asp Asn Val Ala His Gln Ile Ser
        115                 120                 125

Ala Ser Trp Gly Glu Ser Glu Ser Leu Ile Asn Tyr Tyr Val Gln Gln
    130                 135                 140

Gln Met Glu Thr Pro Glu Tyr Ala Glu Thr Phe Asn Gln Leu Phe Met
145                 150                 155                 160

Gln Ala Ala Ala Gln Gly Thr Ser Met Phe Ala Ser Ala Gly Asp Ser
                165                 170                 175

Gly Ala Tyr Asp Ala Ser Gly Asp Leu Asn Thr Tyr Asp Leu Ser Val
            180                 185                 190

Asp Asn Pro Ala Asp Ser Pro Tyr Ile Thr Ala Gly Gly Thr Thr
        195                 200                 205

Val Pro Phe Thr Tyr Thr Ser Thr Gln Tyr Asn Leu Ser Ile Thr Val
    210                 215                 220

Pro Gln Glu Arg Ala Trp Gly Trp Asp Tyr Leu Tyr Pro Leu Phe Asp
225                 230                 235                 240

Ala Arg Gly Leu Asn Asn Pro Thr Gly Trp Ala Gln Arg Tyr Phe Val
                245                 250                 255

Gly Gly Gly Gly Gly Phe Ser Gln Leu Phe Ala Thr Pro Asp Tyr Gln
            260                 265                 270

Thr Gly Val Ser Gly Val Asn Ser Tyr Thr Ala Val His Gln Trp Thr
        275                 280                 285

Pro Ser Ser Asp Phe Thr Ser Val Thr Arg Asp Ala Gln Pro Thr Ile
    290                 295                 300

Val Thr Gly Thr Gly Thr Gly Arg Asn Leu Pro Asp Leu Ser Met Asn
305                 310                 315                 320
```

Ala Asp Pro Tyr Thr Gly Tyr Ser Val Tyr Phe Asn Leu Pro Thr Thr
            325                 330                 335

Asn Gly Ala Thr Thr Val Asp Ser Gly Trp Ala Thr Tyr Gly Gly Thr
            340                 345                 350

Ser Phe Val Ala Pro Gln Leu Ala Gly Leu Ser Ala Leu Ile Asn Ser
            355                 360                 365

Ala Asn Gly Ser Glu Ala Gly Phe Trp Asn Pro Gln Leu Tyr Arg Phe
            370                 375                 380

Ala Gln Ser Asn His Ser Pro Leu His Pro Leu Asn Thr Ala Gly Ala
385                 390                 395                 400

Ser Asn Asp Asn Val Phe Tyr Ser Gly Thr Pro Gly Ala Ile Tyr Asn
            405                 410                 415

Gln Ala Thr Gly Leu Gly Thr Pro Asp Val Thr Ala Leu Ala Gln Ala
            420                 425                 430

Phe Gly Lys
        435

<210> SEQ ID NO 6
<211> LENGTH: 440
<212> TYPE: PRT
<213> ORGANISM: Artificial sequence
<220> FEATURE:
<223> OTHER INFORMATION: Synthetic construct

<400> SEQUENCE: 6

Val Thr Pro Asn Pro Thr Gly Arg Met Thr Asn Asp Leu Val Ser Arg
1               5                   10                  15

Tyr Asn Val Gln Pro Leu Tyr Thr Lys Gly Ala Asn Gly Ser Gly Gln
            20                  25                  30

Thr Ile Gly Ile Val Thr Leu Ala Asp Phe Asn Pro Ser Asp Ala Tyr
        35                  40                  45

Ser Tyr Trp Gln Tyr Asn Asn Ile Asn Val Asn Pro Asn Arg Ile Thr
    50                  55                  60

Lys Ile Asn Val Asp Gly Gly Ser Gly Leu Ser Glu Asp Ala Gly Ser
65                  70                  75                  80

Asp Glu Thr Ser Leu Asp Val Glu Gln Ser Gly Ala Leu Ala Pro Gly
            85                  90                  95

Ala Asn Leu Asn Val Tyr Val Gly Pro Asn Thr Asp Thr Gly Phe Val
            100                 105                 110

Asp Ala Tyr Ala Lys Ala Ile Asn Asp Asn Val Ala His Gln Ile Ser
            115                 120                 125

Ala Ser Trp Gly Glu Ser Glu Ser Leu Ile Asn Tyr Val Gln Gln
            130                 135                 140

Gln Met Glu Thr Pro Glu Tyr Ala Glu Thr Phe Asn Gln Leu Phe Met
145                 150                 155                 160

Gln Ala Ala Ala Gln Gly Thr Ser Met Phe Ala Ser Ala Gly Asp Ser
            165                 170                 175

Gly Ala Tyr Asp Ala Ser Gly Asp Leu Asn Thr Tyr Asp Leu Ser Val
            180                 185                 190

Asp Asn Pro Ala Asp Ser Pro Tyr Ile Thr Ala Ala Gly Gly Thr Thr
            195                 200                 205

Val Pro Phe Thr Tyr Thr Ser Thr Gln Tyr Asn Leu Ser Ile Thr Val
            210                 215                 220

Pro Gln Glu Arg Ala Trp Gly Trp Asp Tyr Leu Tyr Pro Leu Phe Asp
225                 230                 235                 240

```
Ala Arg Gly Leu Asn Asn Pro Thr Gly Trp Ala Gln Arg Tyr Phe Val
            245                 250                 255

Gly Gly Gly Gly Gly Phe Ser Gln Leu Phe Ala Thr Pro Asp Tyr Gln
            260                 265                 270

Thr Gly Val Ser Gly Val Asn Ser Tyr Thr Ala Val His Gln Trp Thr
            275                 280                 285

Pro Ser Ser Asp Phe Thr Ser Val Thr Arg Asp Ala Gln Pro Thr Ile
            290                 295                 300

Val Thr Gly Thr Gly Thr Gly Arg Asn Leu Pro Asp Leu Ser Met Asn
305                 310                 315                 320

Ala Asp Pro Tyr Thr Gly Tyr Ser Val Tyr Phe Asn Leu Pro Thr Thr
            325                 330                 335

Asn Gly Ala Thr Thr Val Asp Ser Gly Trp Ala Thr Tyr Gly Gly Thr
            340                 345                 350

Ser Phe Val Ala Pro Gln Leu Ala Gly Leu Ser Ala Leu Ile Asn Ser
            355                 360                 365

Ala Asn Gly Ser Glu Ala Gly Phe Trp Asn Pro Gln Leu Tyr Arg Phe
370                 375                 380

Ala Gln Ser Asn His Ser Pro Leu His Pro Leu Asn Thr Ala Gly Ala
385                 390                 395                 400

Ser Asn Asp Asn Val Phe Tyr Ser Gly Thr Pro Gly Ala Ile Tyr Asn
            405                 410                 415

Gln Ala Thr Gly Leu Gly Thr Pro Asp Val Thr Ala Leu Ala Gln Ala
            420                 425                 430

Phe Gly Lys His Gln His Gln His
            435                 440
```

```
<210> SEQ ID NO 7
<211> LENGTH: 1596
<212> TYPE: DNA
<213> ORGANISM: Nocardiopsis sp.
<220> FEATURE:
<221> NAME/KEY: CDS
<222> LOCATION: (318)..(1463)
<220> FEATURE:
<221> NAME/KEY: sig_peptide
<222> LOCATION: (318)..(404)
<220> FEATURE:
<221> NAME/KEY: mat_peptide
<222> LOCATION: (900)..(1463)

<400> SEQUENCE: 7
```

```
acgtttggta cgggtaccgg tgtccgcatg tggccagaat gcccccttgc gacagggaac     60
ggattcggtc ggtagcgcat cgactccgac aaccgcgagg tggccgttcg cgtcgccacg    120
ttctgcgacc gtcatgcgac ccatcatcgg gtgaccccac cgagctctga atggtccacc    180
gttctgacgg tcttcccctc accaaaacgt gcacctatgg ttaggacgtt gtttaccgaa    240
tgtctcggtg aacgacaggg gccggacggt attcggcccc gatccccgt tgatccccc     300 aggagagtag ggacccc atg cga ccc tcc ccc  gtt gtc tcc gcc atc  ggt    350
               Met Arg Pro Ser Pro  Val Val Ser Ala Ile  Gly
                    -190                    -185 acg gga gcg ctg  gcc ttc ggt ctg gcg  ctg tcc ggt acc ccg  ggt       395
Thr Gly Ala Leu  Ala Phe Gly Leu Ala  Leu Ser Gly Thr Pro  Gly
             -180                -175                -170 gcc ctc gcg gcc  acc gga gcg ctc ccc  cag tca ccc acc ccg  gag       440
Ala Leu Ala Ala  Thr Gly Ala Leu Pro  Gln Ser Pro Thr Pro  Glu
             -165                -160                -155
```

-continued

| | | |
|---|---|---|
| gcc gac gcg gtc tcc atg cag gag gcg ctc cag cgc gac ctc gac<br>Ala Asp Ala Val Ser Met Gln Glu Ala Leu Gln Arg Asp Leu Asp<br>         -150                      -145                   -140 | 485 |
| ctg acc tcc gcc gag gcc gag gag ctg ctg gcc gcc cag gac acc<br>Leu Thr Ser Ala Glu Ala Glu Glu Leu Leu Ala Ala Gln Asp Thr<br>         -135                      -130                   -125 | 530 |
| gcc ttc gag gtc gac gag gcc gcg gcc gag gcc gcc ggg gac gcc<br>Ala Phe Glu Val Asp Glu Ala Ala Ala Glu Ala Ala Gly Asp Ala<br>         -120                      -115                   -110 | 575 |
| tac ggc ggc tcc gtc ttc gac acc gag agc ctg gaa ctg acc gtc ctg<br>Tyr Gly Gly Ser Val Phe Asp Thr Glu Ser Leu Glu Leu Thr Val Leu<br>         -105                      -100                   -95 | 623 |
| gtc acc gat gcc gcc gcg gtc gag gcc gtg gag gcc acc ggc gcc ggg<br>Val Thr Asp Ala Ala Ala Val Glu Ala Val Glu Ala Thr Gly Ala Gly<br>         -90                      -85                   -80 | 671 |
| acc gag ctg gtc tcc tac ggc atc gac ggt ctc gac gag atc gtc cag<br>Thr Glu Leu Val Ser Tyr Gly Ile Asp Gly Leu Asp Glu Ile Val Gln<br>         -75                      -70                   -65 | 719 |
| gag ctc aac gcc gcc gac gcc gtt ccc ggt gtg gtc ggc tgg tac ccg<br>Glu Leu Asn Ala Ala Asp Ala Val Pro Gly Val Val Gly Trp Tyr Pro<br>-60                  -55                   -50                   -45 | 767 |
| gac gtg gcg ggt gac acc gtc gtc ctg gag gtc ctg gag ggt tcc gga<br>Asp Val Ala Gly Asp Thr Val Val Leu Glu Val Leu Glu Gly Ser Gly<br>          -40                      -35                   -30 | 815 |
| gcc gac gtc agc ggc ctg ctc gcg gac gcc ggc gtg gac gcc tcg gcc<br>Ala Asp Val Ser Gly Leu Leu Ala Asp Ala Gly Val Asp Ala Ser Ala<br>         -25                      -20                   -15 | 863 |
| gtc gag gtg acc acg agc gac cag ccc gag ctc tac gcc gac atc atc<br>Val Glu Val Thr Thr Ser Asp Gln Pro Glu Leu Tyr Ala Asp Ile Ile<br>         -10                      -5                   -1  1 | 911 |
| ggt ggt ctg gcc tac acc atg ggc ggc cgc tgt tcg gtc ggc ttc gcg<br>Gly Gly Leu Ala Tyr Thr Met Gly Gly Arg Cys Ser Val Gly Phe Ala<br>5                   10                   15                   20 | 959 |
| gcc acc aac gcc gcc ggt cag ccc ggg ttc gtc acc gcc ggt cac tgc<br>Ala Thr Asn Ala Ala Gly Gln Pro Gly Phe Val Thr Ala Gly His Cys<br>          25                      30                   35 | 1007 |
| ggc cgc gtg ggc acc cag gtg acc atc ggc aac ggc agg ggc gtc ttc<br>Gly Arg Val Gly Thr Gln Val Thr Ile Gly Asn Gly Arg Gly Val Phe<br>          40                      45                   50 | 1055 |
| gag cag tcc gtc ttc ccc ggc aac gac gcg gcc ttc gtc cgc ggt acg<br>Glu Gln Ser Val Phe Pro Gly Asn Asp Ala Ala Phe Val Arg Gly Thr<br>          55                      60                   65 | 1103 |
| tcc aac ttc acg ctg acc aac ctg gtc agc cgc tac aac acc ggc ggg<br>Ser Asn Phe Thr Leu Thr Asn Leu Val Ser Arg Tyr Asn Thr Gly Gly<br>          70                      75                   80 | 1151 |
| tac gcc acg gtc gcc ggt cac aac cag gcc ccc atc ggc tcc tcc gtc<br>Tyr Ala Thr Val Ala Gly His Asn Gln Ala Pro Ile Gly Ser Ser Val<br>85                  90                   95                   100 | 1199 |
| tgc cgc tcc ggc tcc acc acc ggt tgg cac tgc ggc acc atc cag gcc<br>Cys Arg Ser Gly Ser Thr Thr Gly Trp His Cys Gly Thr Ile Gln Ala<br>          105                      110                   115 | 1247 |
| cgc ggc cag tcg gtg agc tac ccc gag ggc acc gtc acc aac atg acc<br>Arg Gly Gln Ser Val Ser Tyr Pro Glu Gly Thr Val Thr Asn Met Thr<br>          120                      125                   130 | 1295 |
| cgg acc acc gtg tgc gcc gag ccc ggc gac tcc ggc ggc tcc tac atc<br>Arg Thr Thr Val Cys Ala Glu Pro Gly Asp Ser Gly Gly Ser Tyr Ile<br>          135                      140                   145 | 1343 |
| tcc ggc acc cag gcc cag ggc gtg acc tcc ggc ggc tcc ggc aac tgc<br>Ser Gly Thr Gln Ala Gln Gly Val Thr Ser Gly Gly Ser Gly Asn Cys<br>          150                      155                   160 | 1391 |

```
cgc acc ggc ggg acc acc ttc tac cag gag gtc acc ccc atg gtg aac    1439
Arg Thr Gly Gly Thr Thr Phe Tyr Gln Glu Val Thr Pro Met Val Asn
165                 170                 175                 180 tcc tgg ggc gtc cgt ctc cgg acc tgatccccgc ggttccaggc ggaccgacgg   1493
Ser Trp Gly Val Arg Leu Arg Thr
                185 tcgtgacctg agtaccaggc gtccccgccg cttccagcgg cgtccgcacc ggggtgggac   1553 cgggcgtggc cacggcccca cccgtgaccg gaccgcccgg cta                     1596
```

<210> SEQ ID NO 8
<211> LENGTH: 382
<212> TYPE: PRT
<213> ORGANISM: Nocardiopsis sp.

<400> SEQUENCE: 8

```
Met Arg Pro Ser Pro  Val Val Ser Ala Ile  Gly Thr Gly Ala Leu
               -190               -185              -180

Ala Phe Gly Leu Ala  Leu Ser Gly Thr Pro  Gly Ala Leu Ala Ala
               -175               -170              -165

Thr Gly Ala Leu Pro  Gln Ser Pro Thr Pro  Glu Ala Asp Ala Val
               -160               -155              -150

Ser Met Gln Glu Ala  Leu Gln Arg Asp Leu  Asp Leu Thr Ser Ala
               -145               -140              -135

Glu Ala Glu Glu Leu  Leu Ala Ala Gln Asp  Thr Ala Phe Glu Val
               -130               -125              -120

Asp Glu Ala Ala Ala  Glu Ala Ala Gly Asp  Ala Tyr Gly Gly Ser
               -115               -110              -105

Val Phe Asp Thr Glu  Ser Leu Glu Leu Thr  Val Leu Val Thr Asp Ala
               -100                -95               -90

Ala Ala Val Glu Ala  Val Glu Ala Thr Gly  Ala Gly Thr Glu Leu Val
                -85                -80               -75

Ser Tyr Gly Ile Asp  Gly Leu Asp Glu Ile  Val Gln Glu Leu Asn Ala
           -70                -65                -60

Ala Asp Ala Val Pro  Gly Val Val Gly Trp  Tyr Pro Asp Val Ala Gly
      -55                -50                -45

Asp Thr Val Val Leu  Glu Val Leu Glu Gly  Ser Gly Ala Asp Val Ser
-40                  -35                -30                -25

Gly Leu Leu Ala Asp  Ala Gly Val Asp Ala  Ser Ala Val Glu Val Thr
               -20                -15                -10

Thr Ser Asp Gln Pro  Glu Leu Tyr Ala Asp  Ile Ile Gly Gly Leu Ala
           -5                 -1  1                  5

Tyr Thr Met Gly Gly  Arg Cys Ser Val Gly  Phe Ala Ala Thr Asn Ala
   10                  15                 20

Ala Gly Gln Pro Gly  Phe Val Thr Ala Gly  His Cys Gly Arg Val Gly
25                   30                  35                  40

Thr Gln Val Thr Ile  Gly Asn Gly Arg Gly  Val Phe Glu Gln Ser Val
               45                  50                  55

Phe Pro Gly Asn Asp  Ala Ala Phe Val Arg  Gly Thr Ser Asn Phe Thr
            60                  65                  70

Leu Thr Asn Leu Val  Ser Arg Tyr Asn Thr  Gly Tyr Ala Thr Val
           75                  80                  85

Ala Gly His Asn Gln  Ala Pro Ile Gly Ser  Ser Val Cys Arg Ser Gly
      90                  95                 100

Ser Thr Thr Gly Trp  His Cys Gly Thr Ile  Gln Ala Arg Gly Gln Ser
```

```
                105                 110                 115                 120

Val Ser Tyr Pro Glu Gly Thr Val Thr Asn Met Thr Arg Thr Thr Val
                125                 130                 135

Cys Ala Glu Pro Gly Asp Ser Gly Ser Tyr Ile Ser Gly Thr Gln
                140                 145                 150

Ala Gln Gly Val Thr Ser Gly Ser Gly Asn Cys Arg Thr Gly Gly
                155                 160                 165

Thr Thr Phe Tyr Gln Glu Val Thr Pro Met Val Asn Ser Trp Gly Val
                170                 175                 180

Arg Leu Arg Thr
185

<210> SEQ ID NO 9
<211> LENGTH: 625
<212> TYPE: PRT
<213> ORGANISM: Clostridium-acetobutylicum

<400> SEQUENCE: 9

Met Asn Ser Tyr Val Lys Arg Met Leu Thr Ile Ser Thr Ala Val Phe
1               5                   10                  15

Ile Thr Met Gly Ser Phe Ala Ser Ile Val His Ala Glu Pro Gln Gly
                20                  25                  30

Asp Val Gly Val Thr Glu Gly Val Gly Asp Thr Ile Ala Asn Lys Ala
                35                  40                  45

Ser Phe Leu Gly Asp Leu Asp Pro Asn Thr Gln Val Thr Ile Asp Ile
                50                  55                  60

Val Ile Lys Leu Gln Asn Lys Ser Glu Leu Gln Tyr Ile Asn Asp
65                  70                  75                  80

Thr Val Thr Pro Lys Ser Ser Asn Tyr Arg Arg Tyr Leu Ser Val Ala
                85                  90                  95

Glu Phe Lys Lys Ser Phe Ala Pro Lys Ser Lys Gln Ile Asn Glu Leu
                100                 105                 110

Thr Glu Tyr Leu Lys Ala Phe Gly Ile Lys Ser Glu Val Tyr Gln Asp
                115                 120                 125

Asn Leu Ile Val Thr Ala Thr Gly Thr Ala Asp Gln Ile Asn Lys Ala
                130                 135                 140

Phe Asn Val Glu Leu Lys His Ala Ser Tyr Lys Gly Lys Asn Phe His
145                 150                 155                 160

Ala Ser Lys Lys Gln Pro Lys Leu Pro Lys Lys Ile Ala Asp Asn Ile
                165                 170                 175

Leu Cys Ile Leu Gly Leu Ser Ser Tyr Ser Ser Tyr Thr Thr Lys Thr
                180                 185                 190

Val Lys Val Pro Asn Glu Phe Lys Pro Ser Asn Ser Asn Gly Pro Leu
                195                 200                 205

Ser Leu Asn Pro Ser Asp Leu Ile Lys His Tyr Asn Val Gln Pro Leu
                210                 215                 220

Tyr Lys Asn Gly Ala Ser Gly Lys Asn Glu Ser Ile Gly Ile Val Thr
225                 230                 235                 240

Leu Ala Glu Phe Asn Pro Asn Asp Ala Tyr Ser Phe Trp Lys Gln Glu
                245                 250                 255

Gly Ile Lys Thr Asp Lys Arg Arg Ile Lys Val Ile Asn Val Asp Gly
                260                 265                 270

Gly Ser Gly Asn Asp Gly Ala Asp Glu Thr Thr Leu Asp Val Glu Gln
                275                 280                 285
```

```
Ser Gly Ala Leu Ala Pro Lys Ala Glu Val Asn Val Tyr Val Ala Pro
    290                 295                 300

Asn Thr Asp Pro Gly Phe Val Asp Ala Phe Ala Asn Val Ile Asn Glu
305                 310                 315                 320

Asn Lys Cys His Gln Ile Ser Ala Ser Trp Gly Glu Ser Glu Asp Leu
                325                 330                 335

Ile Ser Tyr Leu Val Ser Gln Gly Gln Glu Thr Lys Gly Tyr Ala Glu
            340                 345                 350

Ala Phe Asn Gln Leu Phe Met Gln Ala Ala Gln Gly Ile Ser Met
        355                 360                 365

Phe Ala Ala Ala Gly Asp Ser Gly Ala Tyr Asp Ser Lys Glu Asn Thr
370                 375                 380

Pro Pro Ser Tyr Glu Leu Ser Val Asp Asn Pro Ala Asp Ser Pro Tyr
385                 390                 395                 400

Ile Thr Ala Ala Gly Gly Thr Thr Leu Ala Trp Gln Gly Thr Val Lys
                405                 410                 415

Glu Thr Ser Val Lys Val Asp Lys Glu Arg Ala Trp Gly Trp Asp Tyr
            420                 425                 430

Leu Tyr Pro Ala Phe Asp Ala Asp Gly Leu Tyr Ser Ser Gly Lys Leu
        435                 440                 445

Asp Lys Tyr Phe Val Gly Gly Gly Gly Phe Ser Lys Ile Phe Asp
450                 455                 460

Thr Pro Asp Tyr Gln Lys Gly Ile Ser Gly Val Asn Arg Phe Thr Gly
465                 470                 475                 480

Val Lys Gln Trp Thr Ala Ser Asn Pro Gln Gly Pro Leu Leu Leu Asn
                485                 490                 495

Val Thr Arg Asp Ala Ala Gln Gln Ile Val Thr Gly Lys Asp Thr Gly
            500                 505                 510

Arg Asn Val Pro Asp Ile Ser Met Asp Ala Asp Pro Tyr Thr Gly Tyr
        515                 520                 525

Asn Val Tyr Met Asn Gly Glu Met Ser Ser Ile Gly Gly Thr Ser Ile
530                 535                 540

Val Ala Pro Gln Leu Ala Gly Leu Cys Ala Leu Ile Asn Asp Asn
545                 550                 555                 560

Asn Thr Gln Val Gly Phe Trp Asn Pro Gln Ile Tyr Lys Phe Ala Gln
                565                 570                 575

Ser Ser Asn Ser Pro Leu Asn Pro Leu Asn Asp Thr Gly Ser Ser Asn
            580                 585                 590

Asp Asn Ile Phe Tyr Thr Ala Thr Lys Gly Thr Ile Tyr Asn Gln Ala
        595                 600                 605

Thr Gly Leu Gly Ile Pro Asp Ile Ala Lys Leu Asn Ala Ser Phe Gly
610                 615                 620

Arg
625

<210> SEQ ID NO 10
<211> LENGTH: 27
<212> TYPE: PRT
<213> ORGANISM: Bacillus lentus

<400> SEQUENCE: 10

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20

```
<210> SEQ ID NO 11
<211> LENGTH: 7
<212> TYPE: PRT
<213> ORGANISM: Artificial sequence
<220> FEATURE:
<223> OTHER INFORMATION: Synthetic construct

<400> SEQUENCE: 11

His Gln His Gln His Gln His
1               5
```

METHODS FOR IMPROVING THE NUTRITIONAL VALUE OF THE ANIMAL FEED USING A PROTEASE

CROSS-REFERENCE TO RELATED APPLICATIONS

This application is a 35 U.S.C. 371 national application of PCT/EP2012/076355 filed Dec. 20, 2012, which claims priority or the benefit under 35 U.S.C. 119 of European application no. 11195932.6 filed Dec. 28, 2011 and U.S. provisional application no. 61/581,684 filed Dec. 30, 2011, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to isolated polypeptides having protease activity and isolated nucleic acid sequences encoding the proteases. The invention also relates to nucleic acid constructs, vectors, and host cells, including plant and animal cells, comprising the nucleic acid sequences, as well as methods for producing and using the proteases, in particular the use of the proteases in animal feed, and detergents.

Background of the Invention

In the use of proteases in animal feed (in vivo), and/or the use of such proteases for treating vegetable proteins (in vitro) it is noted that proteins are essential nutritional factors for animals and humans. Most livestock and many human beings get the necessary proteins from vegetable protein sources. Important vegetable protein sources are e.g. oilseed crops, legumes and cereals.

When e.g. soybean meal is included in the feed of mono-gastric animals such as pigs and poultry, a significant proportion of the soybean meal solids is not digested efficiently (the apparent ileal protein digestibility in piglets, growing pigs and poultry such as broilers, laying hens and roosters is only around 80%).

The gastrointestinal tract of animals consists of a series of segments each representing different pH environments. In mono-gastric animals such as pigs and poultry and many fish the stomach exhibits strongly acidic pH as low as pH 1-2, while the intestine exhibits a more neutral pH in the area pH 6-7. Poultry in addition to stomach and intestine also have a crop preceding the stomach, pH in the crop is mostly determined by the feed ingested and hence typically lies in the range pH 4-6. Protein digestion by a protease may occur along the entire digestive tract, given that the protease is active and survives the conditions in the digestive tract. Hence, proteases which are highly acid stable for survival in the gastric environment and at the same time are efficiently active at broad physiological pH of the target animal are especially desirable.

Also, animal feed is often formulated in pelleted form, where steam is applied in the pelleting process. It is therefore also desireable that proteases used in animal feed are capable to remain active after exposure to steam treatment.

Proteases have also for many years been used in detergent compositions for hydrolysing proteinaceous materials on textiles, hard surfaces and other surfaces, such as the skin, etc. Such detergent compositions can be used for the cleaning of textiles, in hand washing or in automatic machines by powders, tablets or soap bars, and in dish washing by hand or machine as powders, and tablets.

The novel S53 family proteases of the invention are also useful for these purposes.

In order to produce a protease for industrial use, it is important that the protease is produced in high yields making the product available in sufficient quantities in order to be able to provide the protease at a favourable price.

Polypeptides Having Protease Activity

Polypeptides having protease activity, or proteases, are sometimes also designated peptidases, proteinases, peptide hydrolases, or proteolytic enzymes. Proteases may be of the exo-type that hydrolyzes peptides starting at either end thereof, or of the endo-type that act internally in polypeptide chains (endopeptidases). Endopeptidases show activity on N- and C-terminally blocked peptide substrates that are relevant for the specificity of the protease in question.

The term "protease" is defined herein as an enzyme that hydrolyses peptide bonds. This definition of protease also applies to the protease-part of the terms "parent protease" and "protease variant," as used herein. The term "protease" includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1-5 published in Eur. J. Bio-chem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The nomenclature is regularly supplemented and updated; see e.g. the World Wide Web (WWW) at www.chem.qmw.ac.uk/iubmb/enzyme/index.html.

The proteases of the invention and for use according to the invention are selected from the group consisting of:

(a) proteases belonging to the EC 3.4.21. enzyme group; and/or (b) Serine proteases of the peptidase family S53, that comprises two different types of peptidases: tripeptidyl aminopeptidases (exo-type) and endo-peptidases.

As described in Biochem. J. 290:205-218 (1993) and in MEROPS protease database, release 9.4 (31 Jan. 2011) (www.merops.ac.uk). The database is described in Rawlings, N.D., Barrett, A. J. & Bateman, A. (2010) MEROPS: the peptidase database. Nucleic Acids Res 38, D227-D233.

Peptidase family S53 contains acid-acting endopeptidases and tripeptidyl-peptidases.

The residues of the catalytic triad are Glu, Asp, Ser, and there is an additional acidic residue, Asp, in the oxyanion hole. The Ser residue is the nucleophile equivalent to Ser in the Asp, His, Ser triad of subtilisin, and the Glu of the triad is a substitution for the general base His in subtilisin.

Mutation of any of the amino acids of the catalytic triad or oxyanion hole will result in a change or loss of enzyme activity. The amino acids of the catalytic triad and oxyanion hole of the S53 protease from Bacillus sp 19138 (SEQ ID NO: 5) are probably positions Glu-82, Asp-86, Asp-175 and Ser-353.

The peptidases of the S53 family tend to be most active at acidic pH (unlike the homologous subtilisins), and this can be attributed to the functional importance of carboxylic residues, notably Asp in the oxyanion hole.

The amino acid sequences are not closely similar to those in family S8, and this, taken together with the quite different active site residues and the resulting lower pH for maximal activity, provides for a substantial difference to that family.

Protein fold of the peptidase unit for members of this family resembles that of subtilisin, the type example of clan SB.

A new S53 protease from *Bacillus* sp 19138 with high activity at low pH (3-4) on soybean-maize meal was identified and cloned in relation to the present invention.

For determining whether a given protease is a Serine protease, and a family S53 protease, reference is made to the above Handbook and the principles indicated therein. Such determination can be carried out for all types of proteases, be it naturally occurring or wild-type proteases; or genetically engineered or synthetic proteases.

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 15, 20, 25, 30, 35, 37, 40, 45, 50, 55, 60, 65, 70, 80, 90, or 95° C. Examples of protease substrates are collagen, such as Azurine-Crosslinked Collagen (AZCL-collagen), or suc-AAPR-pNA. Examples of suitable protease assays are described in the experimental part.

Description of the Related Art

S53 Proteases isolated from *Bacillus* sp. are known in the art. One example is a *B. coagulans* from which two S53 proteases have been assigned with an identity to SEQ ID NO: 5 of the present invention of 41.3% and 37.2% and *Bacillus* sp. MN-32 with an identity to SEQ ID NO: 5 of the present invention of 39.5%.

In Noelling et al.; 'Genome sequence and comparative analysis of the solvent-producing bacterium *Clostridium acetobutylicum*' J Bacteriol. 183:4823-4838 (2001) a possible periplasmic aspartyl protease having 65.9% identity to SEQ ID NO: 5 of the present invention is disclosed (UNIPROT:Q97LD7, SEQ ID NO: 9). The publication indicates that it is a serine protease. The same sequence with UNIPROT number F0K735 is also disclosed by Hu et al. in 'Comparative genomic and transcriptomic analysis revealed genetic characteristics related to solvent formation and xylose utilization in *Clostridium acetobutylicum* EA 2018', BMC Genomics 12:93-93 (2011) and was furthermore submitted to the EMBL/GenBank/DDBJ databases by Bao, G Li, Y in April 2011 under UNIPROT:F7ZTR3.

In WO 2005/066339 two sequences (SEQ ID NO: 29 and 30) from an *Alicyclusbacillus* sp. strain is disclosed as serine-carboxylic proteases. The sequences have 52.3% identity to SEQ ID NO: 5 of the present invention. The application does not indicate any specific uses of the peptide of SEQ ID NO: 29 or 30, but indicates uses of compositions comprising the various peptides disclosed in detergent, food, baking, brewed products, fruit juices, animal feed, pulping, etc.

The present invention provides polypeptides having protease activity and polynucleotides encoding the polypeptides. The proteases of the invention are serine proteases of the peptidase family S53. The proteases of the invention exhibit pH properties, especially pH stability properties which make them of substantial interest as candidates for use in animal feed and other applications.

The proteases of the invention are acidic proteases with a trypsin-like specificity. The proteases have activity on Suc-Ala-Ala-Pro-Arg-pNA with a broad pH range from 3-6 and retains more than 80% activity after being subjected for 2 hours to pH as low as 3.

The use of proteases in animal feed to improve digestion of proteins in the feed is known. WO 95/28850 discloses the combination of a phytase and one or more microbial proteolytic enzymes to improve the solubility of vegetable proteins. WO 01/58275 discloses the use of acid stable proteases of the subtilisin family in animal feed. WO 01/58276 discloses the use in animal feed of acid-stable proteases related to the protease derived from *Nocardiopsis* sp. NRRL 18262 (the 10R protease), as well as a protease derived from *Nocardiopsis alba* DSM 14010. WO 04/072221, WO 04/111220, WO 04/111223, WO 05/035747, and WO 05/123911 disclose proteases related to the 10R protease and their use in animal feed. Also, WO 04/072279 discloses the use of other proteases.

WO 04/034776 discloses the use of a subtilisin/keratinase, PWD-1 from *B. licheniformis* in the feed of poultry. WO 04/077960 discloses a method of increasing digestibility of a forage or a grain in ruminants by applying a bacterial or fungal protease.

Commercial products comprising a protease and marketed for use in animal feed include RONOZYME® ProAct (DSM NP/Novozymes), Axtra® (Danisco), Avizyme® (Danisco), Porzyme® (Danisco), Allzyme™ (Alltech), Versazyme® (BioResources, Int.), Poultrygrow™ (Jefo) and Cibenza® DP100 (Novus).

SUMMARY OF THE INVENTION

The present invention relates to isolated polypeptides having protease activity selected from the group consisting of:

(a) a polypeptide having at least 80% sequence identity to the polypeptide of SEQ ID NO: 5, SEQ ID NO: 6, or the mature polypeptide of SEQ ID NO: 2 or SEQ ID NO: 4;

(b) a polypeptide encoded by a polynucleotide that hybridizes under high stringency conditions, or very high stringency conditions with
  (i) the mature polypeptide coding sequence of SEQ ID NO: 1,
  (ii) the mature polypeptide coding sequence of SEQ ID NO: 3, or
  (iii) the full-length complementary strand of (i) or (ii);

(c) a polypeptide encoded by a polynucleotide having at least 80% sequence identity to the mature polypeptide coding sequence of SEQ ID NO: 1 or SEQ ID NO: 3;

(d) a variant comprising a substitution, deletion, and/or insertion of one or more (several) amino acids of the polypeptide of SEQ ID NO: 5, SEQ ID NO: 6, or the mature polypeptide of SEQ ID NO: 2 or SEQ ID NO: 4; and (e) a fragment of a polypeptide of (a), (b), (c) or (d), that has protease activity.

The present invention also relates to isolated polynucleotides encoding the polypeptides of the present invention, nucleic acid constructs, recombinant expression vectors, and recombinant host cells comprising the polynucleotides, and to methods of producing the polypeptides.

The present invention also relates to compositions comprising the polypeptide of the invention such as animal feed compositions or detergent compositions as well as animal feed additives comprising the polypeptide of the invention. The present invention further relates to methods for preparing a composition for use in animal feed, for improving the nutritional value of an animal feed, and methods of treating proteins to be used in animal feed compositions.

OVERVIEW OF SEQUENCE LISTING

Figure 1:
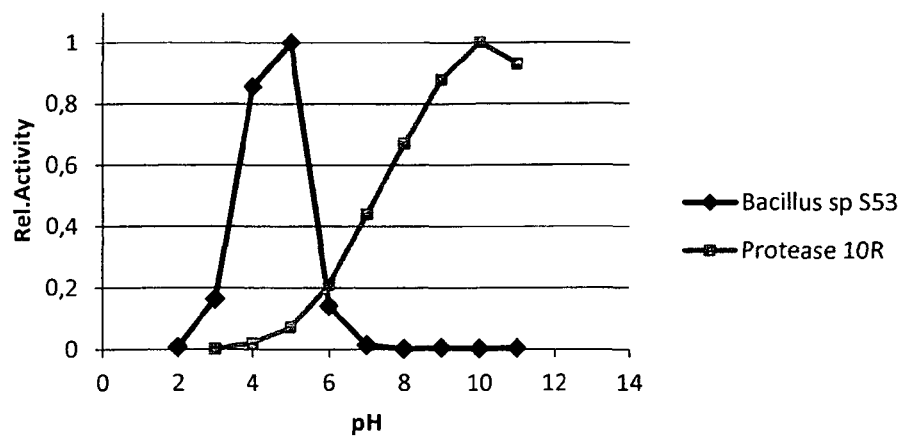
FIG. 1 shows pH-activity profile of the S53 protease from *Bacillus* sp 19138 compared to the 10R protease. Suc-AAPR-pNA was used as substrate for the S53 protease from *Bacillus* sp 19138. Suc-AAPF-pNA was used as substrate for the 10R protease.
Figure 2:
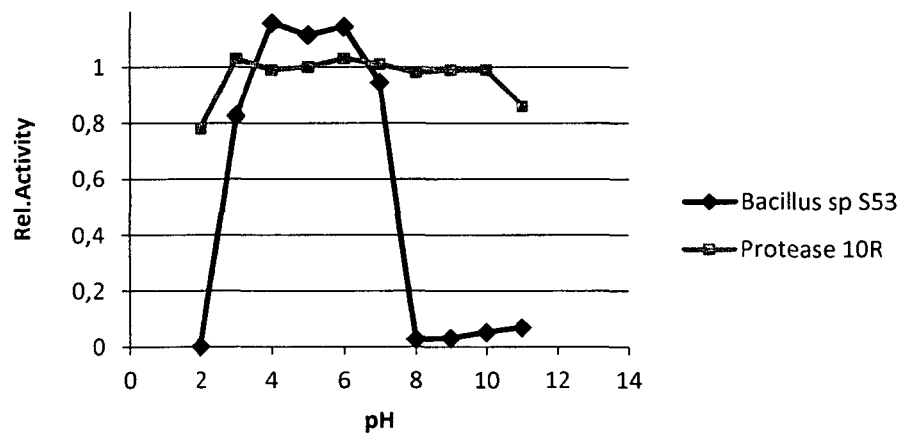
FIG. 2 shows the pH-stability profile (residual activity after 2 hours at 37° C. of the S53 protease from *Bacillus* sp 19138 compared to the 10R protease, FIG. 3 shows the temperature activity profile at pH 4.0 of the S53 protease from *Bacillus* sp 19138 compared to the temperature activity profile at pH 6.5 of the 10R protease, FIG. 4 shows the P1-specificity on 10 Suc-AAPX-pNA substrates at pH 4.0 of the S53 protease from *Bacillus* sp 19138 compared to the P1-specificity on 10 Suc-AAPX-pNA substrates at pH 9.0 of the 10R protease, FIG. 5 shows the relative activity on soybean-maize meal of the S53 protease from *Bacillus* sp 19138 compared to the 10R protease.
Figure 3:
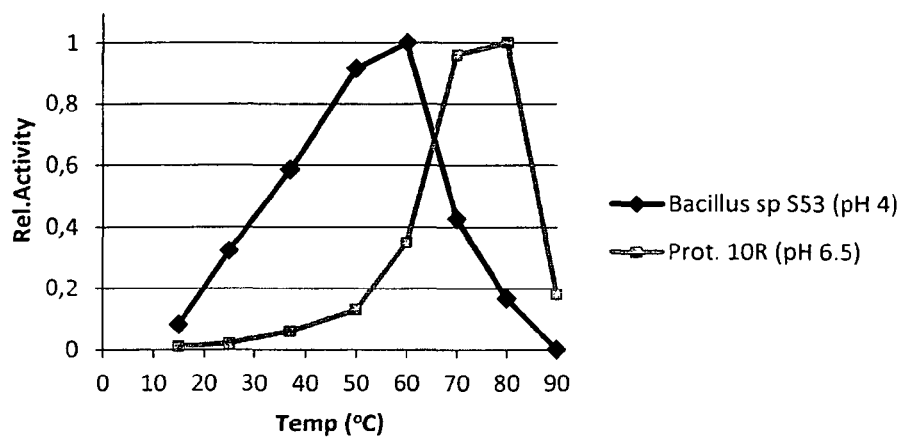
Figure 4:
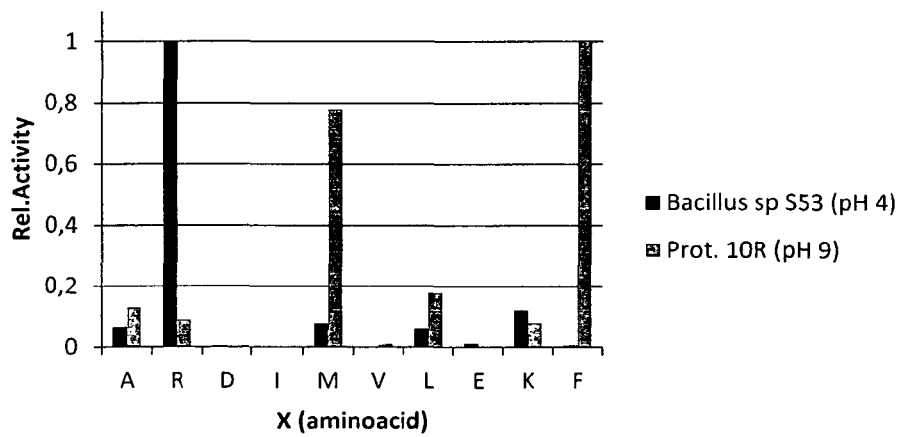

SEQ ID NO: 1 is the DNA sequence as isolated from the *Bacillus* sp 19138.

SEQ ID NO: 2 is the amino acid sequence as deduced from SEQ ID NO: 1.

SEQ ID NO: 3 is the DNA sequence of the recombinant expressed DNA sequence with HQ-tag.

SEQ ID NO: 4 is the amino acid sequence as deduced from SEQ ID NO: 3.

SEQ ID NO: 5 is the amino acid sequence of the mature protease *Bacillus* sp 19138.

SEQ ID NO: 6 is the amino acid sequence of the mature protease obtained from SEQ ID NO. 3.

SEQ ID NO: 7 is the DNA sequence of protease 10R (WO 05/035747, SEQ ID NO: 1).

SEQ ID NO: 8 is the amino acid sequence of protease 10R (WO 05/035747, SEQ ID NO: 2).

SEQ ID NO: 9 is the amino acid sequence from *Clostridium-acetobutylicum* (SWISSPROT:F0K735).

SEQ ID NO: 10 is a *Bacillus lentus* secretion signal.

| IDENTITY MATRIX OF SEQUENCES: | | | | | | |
|---|---|---|---|---|---|---|
| | SEQ ID NO: 2 | SEQ ID NO: 4 | SEQ ID NO: 5 | SEQ ID NO: 6 | SEQ ID NO: 8 | SEQ ID NO: 9 |
| SEQ ID NO: 2 | 100 | 98.1 | 100 | 100 | 33.3 | 58.6 |
| SEQ ID NO: 4 | 98.1 | 100 | 100 | 100 | 33.3 | 59.3 |
| SEQ ID NO: 5 | 100 | 100 | 100 | 100 | 29.6 | 65.9 |
| SEQ ID NO: 6 | 100 | 100 | 100 | 100 | 29.6 | 65.9 |
| SEQ ID NO: 8 | 33.3 | 33.3 | 29.6 | 29.6 | 100 | 28.6 |
| SEQ ID NO: 9 | 58.6 | 59.3 | 65.9 | 65.9 | 28.6 | 100 |

DEFINITIONS

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

Control sequences: The term "control sequences" means all components necessary for the expression of a polynucleotide encoding a polypeptide of the present invention. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of the polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to additional nucleotides that provide for its expression.

Fragment: The term "fragment" means a polypeptide having one or more (several) amino acids deleted from the amino and/or carboxyl terminus of a mature polypeptide; wherein the fragment has protease activity. In one aspect, a fragment contains at least 415 amino acid residues (e.g., amino acids 11-425 of SEQ ID NO: 2), at least 425 amino acid residues (e.g., amino acids 6 to 430 of SEQ ID NO: 2). In another aspect, a fragment contains at least 420 amino acid residues (e.g., amino acids 11-430 of SEQ ID NO: 4), at least 430 amino acid residues (e.g., amino acids 6 to 435 of SEQ ID NO: 4).

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Isolated polynucleotide: The term "isolated polynucleotide" means a polynucleotide that is modified by the hand of man relative to that polynucleotide as found in nature. In one aspect, the isolated polynucleotide is at least 1% pure, e.g., at least 5% pure, more at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

Isolated polypeptide: The term "isolated polypeptide" means a polypeptide that is modified by the hand of man relative to that polypeptide as found in nature. In one aspect, the polypeptide is at least 1% pure, e.g., at least 5% pure, at least 10% pure, at least 20% pure, at least 40% pure, at least 60% pure, at least 80% pure, and at least 90% pure, as determined by SDS-PAGE.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 435 in the numbering of SEQ ID NO: 2, amino acids −204 to −177 of SEQ ID NO: 2 is a signal peptide. In another aspect, the mature polypeptide is amino acids 1 to 442 in the numbering of SEQ ID NO: 4, amino acids −203 to −177 of SEQ ID NO: 4 is a signal peptide.

Mature polypeptide coding sequence: The term "mature polypeptide coding sequence" means a polynucleotide that encodes a mature polypeptide having protease activity. In one aspect, the mature polypeptide coding sequence is nucleotides 613-1917 in the numbering of SEQ ID NO: 1. Further nucleotides 1 to 84 in the numbering of SEQ ID NO: 1 encode a signal peptide. In another aspect, the mature polypeptide coding sequence is nucleotides 610-1929 in the numbering of SEQ ID NO: 3. Further nucleotides 1 to 81 in the numbering of SEQ ID NO: 3 encode a signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Operably linked: The term "operably linked" means a configuration in which a control sequence is placed at an appropriate position relative to the coding sequence of a polynucleotide such that the control sequence directs the expression of the coding sequence.

Protease activity: The term "protease activity" means a proteolytic activity (EC 3.4). Proteases of the invention are endopeptidases (EC 3.4.21). There are several protease activity types: The three main activity types are: trypsin-like where there is cleavage of amide substrates following Arg or Lys at P1, chymotrypsin-like where cleavage occurs following one of the hydrophobic amino acids at P1, and elastase-like with cleavage following an Ala at P1. For purposes of the present invention, protease activity is determined according to the procedure described in "Materials and Methods" below.

The polypeptides of the present invention have at least 20%, e.g., at least 40%, at least 50%, at least 60%, at least 70%, at least 80%, at least 90%, at least 95%, and at least 100% of the protease activity of the mature polypeptide of SEQ ID NO: 5. Alternatively the polypeptides of the present invention have at least 20%, e.g., at least 40%, at least 50%, at least 60%, at least 70%, at least 80%, at least 90%, at least 95%, and at least 100% of the protease activity of the mature polypeptide of SEQ ID NO: 6.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Stringency conditions: The different strigency conditions are defined as follows.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (several) nucleotides deleted from the 5' and/or 3' end of a mature polypeptide coding sequence; wherein the subsequence encodes a fragment having protease activity. In one aspect, a subsequence contains at least 1245 nucleotides (e.g., nucleotides 643 to 1887 of SEQ ID NO: 1), e.g., and at least 1275 nucleotides (e.g., nucleotides 628 to 1902 of SEQ ID NO: 1). In another aspect, a subsequence contains at least 1260 nucleotides (e.g., nucleotides 640 to 1899 of SEQ ID NO: 3), e.g., and at least 1290 nucleotides (e.g., nucleotides 625 to 1914 of SEQ ID NO: 3).

Substantially pure polynucleotide: The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5' and 3' untranslated regions, such as promoters and terminators. Preferably, the polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Variant: The term "variant" means a polypeptide having protease activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

DETAILED DESCRIPTION OF THE INVENTION

Polypeptides Having Protease Activity

The present invention relates to isolated polypeptides having protease activity selected from the group consisting of:

(a) a polypeptide having at least 80% sequence identity to the polypeptide of SEQ ID NO: 5, SEQ ID NO: 6, or the mature polypeptide of SEQ ID NO: 2 or SEQ ID NO: 4;

(b) a polypeptide encoded by a polynucleotide that hybridizes under high stringency conditions, or very high stringency conditions with
   (i) the mature polypeptide coding sequence of SEQ ID NO: 1, and/or
   (ii) the mature polypeptide coding sequence of SEQ ID NO: 3, or
   (iii) the full-length complementary strand of (i) or (ii);

(c) a polypeptide encoded by a polynucleotide having at least 80% sequence identity to the mature polypeptide coding sequence of SEQ ID NO: 1 or SEQ ID NO: 3;

(d) a variant comprising a substitution, deletion, and/or insertion of one or more (several) amino acids of the polypeptide of SEQ ID NO: 5, SEQ ID NO: 6, or the mature polypeptide of SEQ ID NO: 2 or SEQ ID NO: 4; and (e) a fragment of a polypeptide of (a), (b), (c) or (d), that has protease activity.

The present invention relates to isolated polypeptides having a sequence identity to the polypeptide of the mature polypeptide of SEQ ID NO: 2 of at least 80%, e.g., at least 85%, at least 90%, at least 91%, at least 92%, at least 93%, at least 94%, at least 95%, at least 96%, at least 97%, at least 98%, at least 99%, or 100%, which have protease activity. In one aspect, the polypeptides differ by no more than fifty amino acids, e.g., by fortythree amino acids, by forty amino acids, by thirtyfive amino acids, by thirty amino acids, by twentyfive amino acids, by twenty amino acids, by fifteen amino acids, by twelve amino acids, by ten amino acids, by nine amino acids, by eight amino acids, by seven amino acids, by six amino acids, by five amino acids, by four amino acids, by three amino acids, by two amino acids, and by one amino acid from the polypeptide of mature polypeptide of SEQ ID NO:2.

The present invention also relates to the use in animal feed of isolated polypeptides having a sequence identity to the polypeptide the mature polypeptide of SEQ ID NO: 2 of at least 80%, e.g. at least 85%, e.g., at least 87%, at least 89%, at least 90%, at least 91%, at least 92%, at least 93%, at least 94%, at least 95%, at least 96%, at least 97%, at least 98%, at least 99%, or 100%, which have protease activity. In one aspect, the polypeptides differ by no more than fifty amino acids, e.g., by fortythree amino acids, by forty amino acids, by thirtyfive amino acids, by thirty amino acids, by twentyfive amino acids, by twenty amino acids, by fifteen amino acids, by ten amino acids, by eight amino acids, by seven amino acids, by six amino acids, by five amino acids, by four amino acids, by three amino acids, by two amino acids, and by one amino acid from the mature polypeptide of SEQ ID NO: 2.

The present invention further relates to isolated polypeptides having a sequence identity to the polypeptide of the mature polypeptide of SEQ ID NO: 4 of at least 80%, e.g., at least 85%, at least 90%, at least 91%, at least 92%, at least 93%, at least 94%, at least 95%, at least 96%, at least 97%, at least 98%, at least 99%, or 100%, which have protease activity. In one aspect, the polypeptides differ by no more than fifty amino acids, e.g., by fortythree amino acids, by forty amino acids, by thirtyfive amino acids, by thirty amino acids, by twentyfive amino acids, by twenty amino acids, by fifteen amino acids, by twelve amino acids, by ten amino acids, by nine amino acids, by eight amino acids, by seven amino acids, by six amino acids, by five amino acids, by four amino acids, by three amino acids, by two amino acids, and by one amino acid from the polypeptide of mature polypeptide of SEQ ID NO:4.

The present invention also relates to the use in animal feed of isolated polypeptides having a sequence identity to the polypeptide the mature polypeptide of SEQ ID NO: 4 of at least 80%, e.g. at least 85%, e.g., at least 87%, at least 89%, at least 90%, at least 91%, at least 92%, at least 93%, at least 94%, at least 95%, at least 96%, at least 97%, at least 98%, at least 99%, or 100%, which have protease activity. In one aspect, the polypeptides differ by no more fifty amino acids, e.g., by fortythree amino acids, by forty amino acids, by thirtyfive amino acids, by thirty amino acids, by twentyfive acids, by twenty amino acids, by fifteen amino acids, by ten amino acids, by eight amino acids, by seven amino acids, by six amino acids, by five amino acids, by four amino acids, by three amino acids, by two amino acids, and by one amino acid from the mature polypeptide of SEQ ID NO: 4.

An embodiment of the invention is a polypeptide or a polypeptide encoded by a polynucleotide having at least 80% sequence identity to the polypeptide of SEQ ID NO: 5.

An embodiment of the invention is a polypeptide or a polypeptide encoded by a polynucleotide having at least 85% sequence identity to the polypeptide of SEQ ID NO: 5.

An embodiment of the invention is a polypeptide or a polypeptide encoded by a polynucleotide having at least 90% sequence identity to the polypeptide of SEQ ID NO: 5.

An embodiment of the invention is a polypeptide or a polypeptide encoded by a polynucleotide having at least 91% sequence identity to the polypeptide of SEQ ID NO: 5.

An embodiment of the invention is a polypeptide or a polypeptide encoded by a polynucleotide having at least 92% sequence identity to the polypeptide of SEQ ID NO: 5.

An embodiment of the invention is a polypeptide or a polypeptide encoded by a polynucleotide having at least 93% sequence identity to the polypeptide of SEQ ID NO: 5.

An embodiment of the invention is a polypeptide or a polypeptide encoded by a polynucleotide having at least 94% sequence identity to the polypeptide of SEQ ID NO: 5.

An embodiment of the invention is a polypeptide or a polypeptide encoded by a polynucleotide having at least 95% sequence identity to the polypeptide of SEQ ID NO: 5.

An embodiment of the invention is a polypeptide or a polypeptide encoded by a polynucleotide having at least 96% sequence identity to the polypeptide of SEQ ID NO: 5.

An embodiment of the invention is a polypeptide or a polypeptide encoded by a polynucleotide having at least 97% sequence identity to the polypeptide of SEQ ID NO: 5.

An embodiment of the invention is a polypeptide or a polypeptide encoded by a polynucleotide having at least 98% sequence identity to the polypeptide of SEQ ID NO: 5.

An embodiment of the invention is a polypeptide or a polypeptide encoded by a polynucleotide having at least 99% sequence identity to the polypeptide of SEQ ID NO: 5.

An embodiment of the invention is a polypeptide or a polypeptide encoded by a polynucleotide having 100% sequence identity to the polypeptide of SEQ ID NO: 5.

The present invention also relates to the use in animal feed of isolated polypeptides having a sequence identity to the polypeptide of SEQ ID NO: 5 of at least 80%, e.g. at least 85%, e.g., at least 87%, at least 89%, at least 90%, at least 91%, at least 92%, at least 93%, at least 94%, at least 95%, at least 96%, at least 97%, at least 98%, at least 99%, or 100%, which have protease activity. In one aspect, the polypeptides differ by no more fifty amino acids, e.g., by fortythree amino acids, by forty amino acids, by thirtyfive amino acids, by thirty amino acids, by twentyfive acids, by twenty amino acids, by fifteen amino acids, by ten amino acids, by eight amino acids, by seven amino acids, by six amino acids, by five amino acids, by four amino acids, by three amino acids, by two amino acids, and by one amino acid from the polypeptide of SEQ ID NO: 5.

An embodiment of the invention is a polypeptide or a polypeptide encoded by a polynucleotide having at least 80% sequence identity to the polypeptide of SEQ ID NO: 6.

An embodiment of the invention is a polypeptide or a polypeptide encoded by a polynucleotide having at least 85% sequence identity to the polypeptide of SEQ ID NO: 6.

An embodiment of the invention is a polypeptide or a polypeptide encoded by a polynucleotide having at least 90% sequence identity to the polypeptide of SEQ ID NO: 6.

An embodiment of the invention is a polypeptide or a polypeptide encoded by a polynucleotide having at least 91% sequence identity to the polypeptide of SEQ ID NO: 6.

An embodiment of the invention is a polypeptide or a polypeptide encoded by a polynucleotide having at least 92% sequence identity to the polypeptide of SEQ ID NO: 6.

An embodiment of the invention is a polypeptide or a polypeptide encoded by a polynucleotide having at least 93% sequence identity to the polypeptide of SEQ ID NO: 6.

An embodiment of the invention is a polypeptide or a polypeptide encoded by a polynucleotide having at least 94% sequence identity to the polypeptide of SEQ ID NO: 6.

An embodiment of the invention is a polypeptide or a polypeptide encoded by a polynucleotide having at least 95% sequence identity to the polypeptide of SEQ ID NO: 6.

An embodiment of the invention is a polypeptide or a polypeptide encoded by a polynucleotide having at least 96% sequence identity to the polypeptide of SEQ ID NO: 6.

An embodiment of the invention is a polypeptide or a polypeptide encoded by a polynucleotide having at least 97% sequence identity to the polypeptide of SEQ ID NO: 6.

An embodiment of the invention is a polypeptide or a polypeptide encoded by a polynucleotide having at least 98% sequence identity to the polypeptide of SEQ ID NO: 6.

An embodiment of the invention is a polypeptide or a polypeptide encoded by a polynucleotide having at least 99% sequence identity to the polypeptide of SEQ ID NO: 6.

An embodiment of the invention is a polypeptide or a polypeptide encoded by a polynucleotide having 100% sequence identity to the polypeptide of SEQ ID NO: 6.

The present invention also relates to the use in animal feed of isolated polypeptides having a sequence identity to the polypeptide of SEQ ID NO: 6 of at least 80%, e.g. at least 85%, e.g., at least 87%, at least 89%, at least 90%, at least 91%, at least 92%, at least 93%, at least 94%, at least 95%, at least 96%, at least 97%, at least 98%, at least 99%, or 100%, which have protease activity. In one aspect, the polypeptides differ by no fifty amino acids, e.g., by fortythree amino acids, by forty amino acids, by thirtyfive amino acids, by thirty amino acids, by twentyfive acids, by twenty amino acids, by fifteen amino acids, by ten amino acids, by eight amino acids, by seven amino acids, by six amino acids, by five amino acids, by four amino acids, by three amino acids, by two amino acids, and by one amino acid from the polypeptide of SEQ ID NO: 6.

A polypeptide of the present invention preferably comprises or consists of the amino acid sequence of SEQ ID NO: 2 or an allelic variant thereof; or is a fragment fragment missing e.g. 30, 25, 20, 15, 10 or 5 amino acids from the N- and/or C-terminal and having protease activity. In another preferred aspect, the polypeptide comprises or consists of amino acids 1 to 435 of SEQ ID NO: 2.

A polypeptide of the present invention preferably comprises or consists of the amino acid sequence of SEQ ID NO: 4 or an allelic variant thereof; or is a fragment fragment missing e.g. 30, 25, 20, 15, 10 or 5 amino acids from the N- and/or C-terminal and having protease activity. In another preferred aspect, the polypeptide comprises or consists of amino acids 1 to 442 of SEQ ID NO: 4.

A polypeptide of the present invention preferably comprises or consists of the amino acid sequence of SEQ ID NO: 5 or an allelic variant thereof; or is a fragment fragment missing e.g. 30, 25, 20, 15, 10 or 5 amino acids from the N- and/or C-terminal and having protease activity. In another preferred aspect, the polypeptide comprises or consists of amino acids 1 to 435 of SEQ ID NO: 5.

A polypeptide of the present invention preferably comprises or consists of the amino acid sequence of SEQ ID NO: 6 or an allelic variant thereof; or is a fragment fragment missing e.g. 30, 25, 20, 15, 10 or 5 amino acids from the N- and/or C-terminal and having protease activity. In another preferred aspect, the polypeptide comprises or consists of amino acids 1 to 442 of SEQ ID NO: 6.

The present invention also relates to isolated polypeptides having protease activity that are encoded by polynucleotides that hybridize under high stringency conditions, or very high stringency conditions with (i) the mature polypeptide coding sequence of SEQ ID NO: 1, (ii) the mature polypeptide coding sequence of SEQ ID NO: 3, or (iii) the full-length complementary strand of (i) or (ii) (J. Sambrook, E. F. Fritsch, and T. Maniatis, 1989, Molecular Cloning, A Laboratory Manual, 2d edition, Cold Spring Harbor, N.Y.).

The polynucleotide of SEQ ID NO: 1 or SEQ ID NO: 3; or a subsequence thereof, as well as the amino acid sequence of SEQ ID NO: 5, SEQ ID NO: 6, or the mature polypeptide of SEQ ID NO: 2 or SEQ ID NO: 4 or a fragment thereof, may be used to design nucleic acid probes to identify and clone DNA encoding polypeptides having protease activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having protease activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1 or SEQ ID NO: 3; or a subsequence thereof, the carrier material is preferably used in a Southern blot.

For purposes of the present invention, hybridization indicates that the polynucleotide hybridizes to a labeled nucleic acid probe corresponding to the mature polypeptide coding sequence of SEQ ID NO: 1 or the mature polypeptide coding sequence of SEQ ID NO: 3; its full-length complementary strand; or a subsequence thereof; under medium to very high stringency conditions. Molecules to which the nucleic acid probe hybridizes under these conditions can be detected using, for example, X-ray film.

In one aspect, the nucleic acid probe is the mature polypeptide coding sequence of SEQ ID NO: 1 or SEQ ID NO: 3. In another aspect, the nucleic acid probe is a fragment thereof. In another aspect, the nucleic acid probe is a polynucleotide that encodes the polypeptide of SEQ ID NO: 5, SEQ ID NO: 6, the mature polypeptide of SEQ ID NO: 2 or SEQ ID NO: 4, or a fragment thereof. In another preferred aspect, the nucleic acid probe is SEQ ID NO: 1 or SEQ ID NO: 3.

For long probes of at least 100 nucleotides in length, high to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci.*

USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

The present invention also relates to isolated polypeptides having protease activity encoded by polynucleotides having a sequence identity to the mature polypeptide coding sequence of SEQ ID NO: 1 of at least 80%, e.g., at least 85%, at least 90%, at least 91%, at least 92%, at least 93%, at least 94%, at least 95%, at least 96%, at least 97%, at least 98%, at least 99%, or 100%.

The present invention further relates to isolated polypeptides having protease activity encoded by polynucleotides having a sequence identity to the mature polypeptide coding sequence of SEQ ID NO: 3 of at least 80%, e.g., at least 85%, at least 90%, at least 91%, at least 92%, at least 93%, at least 94%, at least 95%, at least 96%, at least 97%, at least 98%, at least 99%, or 100%.

In particular embodiments, the parent proteases and/or the protease variants of the invention and for use according to the invention are selected from the group consisting of:

(a) Proteases belonging to the EC 3.4.21 enzyme group; and (b) Serine proteases of peptidase family S53; as described in Biochem. J. 290:205-218 (1993) and in MEROPS protease database, release 9.5 (www.merops.ac.uk). The database is described in Rawlings, N. D., Barrett, A. J. & Bateman, A. (2010) MEROPS: the peptidase database. Nucleic Acids Res 38, D227-D233.

For determining whether a given protease is a Serine protease, and a family S53 pro-tease, reference is made to the above Handbook and the principles indicated therein. Such determination can be carried out for all types of proteases, be it naturally occurring or wild-type proteases; or genetically engineered or synthetic proteases.

The present invention also relates to variants comprising a substitution, deletion, and/or insertion of one or more (or several) amino acids of the polypeptide of SEQ ID NO: 2 or a homologous sequence thereof. Alternatively, the present invention also relates to a variant of the polypeptide of SEQ ID NO: 2 comprising a substitution, deletion, and/or insertion at one or more (several) positions. The total number of amino acid substitutions, deletions and/or insertions of the polypeptide of SEQ ID NO: 2 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50.

The present invention also relates to variants comprising a substitution, deletion, and/or insertion of one or more (or several) amino acids of the polypeptide of SEQ ID NO: 4 or a homologous sequence thereof. Alternatively, the present invention also relates to a variant of the polypeptide of SEQ ID NO: 4 comprising a substitution, deletion, and/or insertion at one or more (several) positions. The total number of amino acid substitutions, deletions and/or insertions of the polypeptide of SEQ ID NO: 4 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50

The present invention also relates to variants comprising a substitution, deletion, and/or insertion of one or more (or several) amino acids of the polypeptide of SEQ ID NO: 5 or a homologous sequence thereof. Alternatively, the present invention also relates to a variant of the polypeptide of SEQ ID NO: 5 comprising a substitution, deletion, and/or insertion at one or more (several) positions. The total number of amino acid substitutions, deletions and/or insertions of the polypeptide of SEQ ID NO: 5 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50

The present invention also relates to variants comprising a substitution, deletion, and/or insertion of one or more (or several) amino acids of the polypeptide of SEQ ID NO: 6 or a homologous sequence thereof. Alternatively, the present invention also relates to a variant of the polypeptide of SEQ ID NO: 6 comprising a substitution, deletion, and/or insertion at one or more (several) positions. The total number of amino acid substitutions, deletions and/or insertions of the polypeptide of SEQ ID NO: 6 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50

Preferably, amino acid changes are of a minor nature, that is conservative amino acid substitutions, deletions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like. Essential amino acids in a parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identities of essential amino acids can also be inferred from analysis of identities with polypeptides that are related to the parent polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be hybrid polypeptide in which a portion of one polypeptide is fused at the N-terminus or the C-terminus of a portion of another polypeptide.

The polypeptide may be a fused polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure*, Function, and Genetics 6: 240-248; and Stevens, 2003, *Drug Discovery World* 4: 35-48.

The polypeptide may be expressed by a recombinant DNA sequence containing the coding for a His-tag or HQ-tag to give, after any post-translational modifications, the mature polypeptide containing all or part of the His- or HQ-tag. The HQ-tag, having the sequence -RHQHQHQ, may be fully or partly cleaved off the polypeptide during the post-translational modifications resulting in for example the additional amino acids such as -RHQHQH, -RHQHQ, -RHQH, -RHQ, -RH or -R attached to the N-terminal of the mature polypeptide. The His-tag, having the sequence -RPHHHHHH, may be fully or partly cleaved off the polypeptide during the post-translational modifications resulting in additional amino acids such as -RPHHHHH, -RPHHHH, -RPHHH, -RPHH, -RPH, -RP or -R attached to the N-terminal of the mature polypeptide.

Embodiments

In certain embodiments of the invention, the protease of the invention exhibits beneficial thermal properties such as thermostability, steam stability, etc and/or pH properties, such as acid stability, pH optimum, etc.

An embodiment of the invention is isolated polypeptides having improved protease activity between pH 3 and 5, such as between pH 4 and 5, such as pH 3, such as pH 4, such as pH 5, at 25° C. compared to protease 10R.

A further embodiment of the invention is isolated polypeptides having improved protease activity at between 15° C. and 60° C., such as between 25° C. and 50° C., such as at 15° C., at 25° C., at 37° C., at 50° C. or at 60° C. compared to protease 10R.

An additional embodiment of the invention is improved protease activity on soybean-maze meal between pH 3.0 and 5.0, such as at pH 3.0, at pH 4.0 or at pH 5.0 at 40° C. compared to protease 10R.

Another embodiment of the invention is improved protein degrading activity of broiler digesta expressed as the level of free alpha-amino groups in the gizzard after 1 hour at 40° C. when compared to black (no protease present).

Acidity/Alkalinity Properties

In certain embodiments of the invention the protease of the invention exhibits beneficial properties in respect of pH, such as acid stability, pH optimum, etc. Stability of the protease at a low pH is beneficial since the protease can have activity in the intestine after passing through the stomach. In one embodiment of the invention the protease retains >80% activity after 2 hours at pH 3 as determined using the method described in Example 3.

Temperature-Activity

The temperature-activity profile of the protease may be determined as described in Example 3. Activity at low temperatures (30-40° C.) can be advantageous for the digestion of proteins in an animal.

In one embodiment, the invention comprises of a protease having a temperature activity profile at pH 4.0 with relative activity of 0.20 or higher at 25° C., or relative activity of 0.50 or higher at 37° C. when compared to the activity of the protease at 60° C. (cf. Example 3).

Thermostability

Thermostability may be determined as described in Example 8, i.e. using DSC measurements to determine the denaturation temperature, $T_d$, of the purified protease protein. The Td is indicative of the thermostability of the protein: The higher the $T_d$, the higher the thermostability. Accordingly, in a preferred embodiment, the protease of the invention has a $T_d$ which is higher than the $T_d$ of a reference protease, wherein $T_d$ is determined on purified protease samples (preferably with a purity of at least 90% or 95%, as determined by SDS-PAGE).

In preferred embodiments, the thermal properties such as heat-stability, temperature stability, thermostability, steam stability, and/or pelleting stability as provided by the residual activity, denaturation temperature $T_d$, or other parameter of the protease of the invention is higher than the corresponding value, such as the residual activity or $T_d$, of the protease of SEQ ID NO:6, more preferably at least 101% thereof, or at least 102%, 103%, 104%, 105%, 106%, 107%, 108%, 109%, or at least 110% thereof. Even more preferably, the value of the parameter, such as residual activity or $T_d$, of the protease of the invention is at least 120%, 130%, 140%, 150%, 160%, 170%, 180%, or at least 190% of the value for the protease of SEQ ID NO:6.

In still further particular embodiments, the thermostable protease of the invention has a melting temperature, $T_m$ (or a denaturation temperature, $T_d$), as determined using Differential Scanning calorimetry (DSC) as described in example 10 (i.e. in 20 mM sodium acetate, pH 4.0), of at least 50° C. In still further particular embodiments, the $T_m$ is at least 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100° C.

Steam Stability

Steam stability may be determined as described in Example 9 by determining the residual activity of protease molecules after steam treatment at 85° C. or 90° C. for a short time.

Pelleting Stability

Pelleting stability may be determined as described in Example 10 by using enzyme granulate pre-mixed with feed. From the mixer the feed is conditioned with steam to 95° C. After conditioning the feed is pressed to pellets and the residual activity determined.

Sources of Polypeptides Having Protease Activity

A polypeptide having protease activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. For example, the polypeptide may be a polypeptide having protease activity from a gram-positive bacterium within a phylum such as Bacillus, Firmicutes or Actinobacteria or from a gram-negative bacterium within a phylum such as Proteobacteria.

In one aspect, the polypeptide is a protease from a bacterium of the class Bacilli, such as from the order Bacillales, or from the genus *Bacillus* or the species *Bacillus* sp. 19138.

Strains of these taxa are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) using the above-mentioned probes. Techniques for isolating microorganisms from natural habitats are well known in the art. The polynucleotide encoding the polypeptide may then be obtained by similarly screening a genomic or cDNA library of another microorganism or mixed DNA sample. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Polynucleotides

The present invention also relates to isolated polynucleotides encoding a polypeptide of the present invention.

The techniques used to isolate or clone a polynucleotide encoding a polypeptide are known in the art and include isolation from genomic DNA, preparation from cDNA, or a combination thereof. The cloning of the polynucleotides from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Bacillus* sp., or another or related organism from the order Bacillales and thus, for example, may be an allelic or species variant of the polypeptide encoding region of the polynucleotide.

The present invention also relates to isolated polynucleotides comprising or consisting of polynucleotides having a degree of sequence identity to the mature polypeptide coding sequence of SEQ ID NO: 1 or SEQ ID NO: 3 of at least 80%, e.g., at least 85%, at least 90%, at least 91%, at least 92%, at least 93%, at least 94%, at least 95%, at least 96%, at least 97%, at least 98%, at least 99%, or 100%, which encode a polypeptide having protease activity.

Modification of a polynucleotide encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant may be constructed on the basis of the polynucleotide presented as the mature polypeptide coding sequence of SEQ ID NO: 1 or SEQ ID NO: 3, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

The present invention also relates to isolated polynucleotides encoding polypeptides of the present invention, which hybridize under high stringency conditions, or very high stringency conditions with (i) the mature polypeptide coding sequence of SEQ ID NO: 1 or SEQ ID NO: 3, (ii the genomic DNA sequence comprising the mature polypeptide coding sequence of SEQ ID NO: 1 or SEQ ID NO: 3, or (iii) the full-length complementary strand of (i) or (ii); or allelic variants and subsequences thereof (Sambrook et al., 1989, supra), as defined herein.

In one aspect, the polynucleotide comprises or consists of SEQ ID NO: 1 or SEQ ID NO: 3, the mature polypeptide coding sequence of SEQ ID NO: 1 or SEQ ID NO: 3, or a subsequence of SEQ ID NO: 1 or SEQ ID NO: 3 that encodes a fragment of SEQ ID NO: 2 or SEQ ID NO. 4 having protease activity, such as the polynucleotide of nucleotides 613-1917 of SEQ ID NO: 1 or the polynucleotide of nucleotides 610-1929 of SEQ ID NO: 3.

Nucleic Acid Constructs

The present invention also relates to nucleic acid constructs comprising a polynucleotide of the present invention operably linked to one or more (several) control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, a polynucleotide that is recognized by a host cell for expression of a polynucleotide encoding a polypeptide of the present invention. The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American,* 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter including a gene encoding a neutral alpha-amylase in Aspergilli in which the untranslated leader has been replaced by an untranslated leader from a gene encoding triose phosphate isomerase in Aspergilli; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the host cell of choice may be used.

Preferred leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (several) convenient restriction sites to allow for insertion or substitution of the polynucleotide encoding the polypeptide at such sites. Alternatively, the polynucleotide may be expressed by inserting the polynucleotide or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more (several) control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any gram-positive or gram-negative bacterium. Gram-positive bacteria include, but are not limited to, *Bacillus*, *Brevibacillus*, *Clostridium*, *Geobacillus*, *Lactobacillus*, *Lactococcus*, *Paenibacillus*, and *Streptomyces*. Gram-negative bacteria include, but are not limited to *E. coli*, and *Pseudomonas*.

The bacterial host cell may be any Bacillales cell including, but not limited to, *Bacillus amyloliquefaciens*, *Brevibacillus brevis*, *Bacillus circulans*, *Bacillus clausii*, *Bacillus coagulans*, *Bacillus lentus*, *Bacillus licheniformis*, *Geobacillus stearothermophilus*, *Bacillus subtilis*, and *Bacillus thuringiensis* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-207, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

The yeast host cell may be a *Candida*, *Hansenula*, *Kluyveromyces*, *Pichia*, *Saccharomyces*, *Schizosaccharomyces*, or *Yarrowia* cell such as a *Kluyveromyces lactis*, *Sac-*

*charomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023 and Yelton et al., 1984, *Proc. Natl. Acad. Sci. USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Bacillus*. In a more preferred aspect, the cell is *Bacillus* sp-19138.

The present invention also relates to methods of producing a polypeptide of the present invention, comprising: (a) cultivating a recombinant host cell of the present invention under conditions conducive for production of the polypeptide; and (b) recovering the polypeptide.

The host cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

More details are provided in the Section on "Nucleic Acid Constructs, Expression Vectors, Recombinant Host Cells, and Methods for Production of Proteases" below.

The polypeptide may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

In an alternative aspect, the polypeptide is not recovered, but rather a host cell of the present invention expressing a polypeptide is used as a source of the polypeptide.

Plants

The present invention also relates to plants, e.g., a transgenic plant, plant part, or plant cell, comprising an isolated polynucleotide of the present invention so as to express and produce the polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide may be constructed in accordance with methods known in the art. In short, the plant or plant cell is constructed by incorporating one or more (several) expression constructs encoding a polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Mol. Biol.* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods for use in accordance with the present disclosure include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct prepared according to the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention, or a portion of a DNA construct prepared in accordance with the present invention. Crossing results in the introduction of a transgene into a plant line by cross pollinating a starting line with a donor plant line. Non-limiting examples of such steps are further articulated in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising: (a) cultivating a transgenic plant or a plant cell comprising a polynucleotide encoding the polypeptide under conditions conducive for production of the polypeptide; and (b) recovering the polypeptide.

Compositions

The present invention also relates to compositions comprising a protease of the present invention. Preferably, the compositions are enriched in such a protease. The term "enriched" indicates that the protease activity of the composition has been increased, e.g., with an enrichment factor of at least 1.1.

The composition may comprise a protease of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by microorganisms such as bacteria or fungi or by plants or by animals. The compositions may be prepared in accordance with methods known in the art and may be in the form of a liquid or a dry composition. For instance, the composition may be in the form of a granulate or a micro-granulate. The protease may be stabilized in accordance with methods known in the art.

Uses

The present invention is also directed to methods for using the polypeptides having protease activity, or compositions thereof.

Use in Animal Feed

The present invention is also directed to methods for using the proteases having protease activity in animal feed, as well as to feed compositions and feed additives comprising the proteases of the invention.

The term animal includes all animals, including human beings. Examples of animals are non-ruminants, and ruminants. Ruminant animals include, for example, animals such as sheep, goats, and cattle, e.g. beef cattle, cows, and young calves. In a particular embodiment, the animal is a non-ruminant animal. Non-ruminant animals include mono-gastric animals, e.g. pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), young calves; and fish (including but not limited to salmon, trout, tilapia, catfish and carps; and crustaceans (including but not limited to shrimps and prawns).

The term feed or feed composition means any compound, preparation, mixture, or composition suitable for, or intended for intake by an animal.

In the use according to the invention the protease can be fed to the animal before, after, or simultaneously with the diet. The latter is preferred.

In a particular embodiment, the protease, in the form in which it is added to the feed, or when being included in a feed additive, is well-defined. Well-defined means that the protease preparation is at least 50% pure as determined by Size-exclusion chromatography (see Example 12 of WO 01/58275). In other particular embodiments the protease preparation is at least 60, 70, 80, 85, 88, 90, 92, 94, or at least 95% pure as determined by this method.

A well-defined protease preparation is advantageous. For instance, it is much easier to dose correctly to the feed a protease that is essentially free from interfering or contaminating other proteases. The term dose correctly refers in particular to the objective of obtaining consistent and constant results, and the capability of optimising dosage based upon the desired effect.

For the use in animal feed, however, the protease need not be that pure; it may e.g. include other enzymes, in which case it could be termed a protease preparation.

The protease preparation can be (a) added directly to the feed (or used directly in a protein treatment process), or (b) it can be used in the production of one or more intermediate compositions such as feed additives or premixes that is subsequently added to the feed (or used in a treatment process). The degree of purity described above refers to the purity of the original protease preparation, whether used according to (a) or (b) above.

Protease preparations with purities of this order of magnitude are in particular obtainable using recombinant methods of production, whereas they are not so easily obtained and also subject to a much higher batch-to-batch variation when the protease is produced by traditional fermentation methods.

Such protease preparation may of course be mixed with other enzymes.

The protein may be an animal protein, such as meat and bone meal, feather meal, and/or fish meal; or it may be a vegetable protein.

The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa.

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

In a particular embodiment of a treatment process the protease(s) in question is affecting (or acting on, or exerting its hydrolyzing or degrading influence on) the proteins, such as vegetable proteins or protein sources. To achieve this, the protein or protein source is typically suspended in a solvent, eg an aqueous solvent such as water, and the pH and temperature values are adjusted paying due regard to the characteristics of the enzyme in question. For example, the treatment may take place at a pH-value at which the activity of the actual protease is at least 5%, 10%, 20%, 30%, 40%, 50%, 60%, 70%, 80%, or at least 90%. Likewise, for example, the treatment may take place at a temperature at which the activity of the actual protease is at least 5%, 10%, 20%, 30%, 40%, 50%, 60%, 70%, 80%, or at least 90%. The above percentage activity indications are relative to the maximum activities. The enzymatic reaction is continued until the desired result is achieved, following which it may or may not be stopped by inactivating the enzyme, e.g. by a heat-treatment step.

In another particular embodiment of a treatment process of the invention, the protease action is sustained, meaning e.g. that the protease is added to the proteins, but its hydrolysing influence is so to speak not switched on until later when desired, once suitable hydrolysing conditions are established, or once any enzyme inhibitors are inactivated, or whatever other means could have been applied to postpone the action of the enzyme.

In one embodiment the treatment is a pre-treatment of animal feed or proteins for use in animal feed, i.e. the proteins are hydrolysed before intake.

The term improving the nutritional value of an animal feed means improving the availability of nutrients in the feed. In this invention improving the nutritional values refers in particular to improving the availability of the protein fraction of the feed, thereby leading to increased protein extraction, higher protein yields, and/or improved protein utilization. When the nutritional value of the feed is increased, the protein and/or amino acid digestibility is increased and the growth rate and/or weight gain and/or feed conversion (i.e. the weight of ingested feed relative to weight gain) of the animal might be improved.

The protease can be added to the feed in any form, be it as a relatively pure protease or in admixture with other components intended for addition to animal feed, i.e. in the form of animal feed additives, such as the so-called premixes for animal feed.

In a further aspect the present invention relates to compositions for use in animal feed, such as animal feed, and animal feed additives, e.g. premixes.

Apart from the protease of the invention, the animal feed additives of the invention contain at least one fat-soluble vitamin, and/or at least one water soluble vitamin, and/or at least one trace mineral, and/or at least one macro mineral.

Further, optional, feed-additive ingredients are colouring agents, e.g. carotenoids such as beta-carotene, astaxanthin, and lutein; stabilisers; growth improving additives and aroma compounds/flavorings, e.g. creosol, anethol, deca-, undeca- and/or dodeca-lactones, ionones, irone, gingerol, piperidine, propylidene phatalide, butylidene phatalide, capsaicin and/or tannin; antimicrobial peptides; polyunsaturated fatty acids (PUFAs); reactive oxygen generating species; also, a support may be used that may contain, for example, 40-50% by weight of wood fibres, 8-10% by weight of stearine, 4-5% by weight of curcuma powder, 4-58% by weight of rosemary powder, 22-28% by weight of limestone, 1-3% by weight of a gum, such as gum arabic, 5-50% by weight of sugar and/or starch and 5-15% by weight of water.

A feed or a feed additive of the invention may also comprise at least one other enzyme selected from amongst phytase (EC 3.1.3.8 or 3.1.3.26); xylanase (EC 3.2.1.8); galactanase (EC 3.2.1.89); alpha-galactosidase (EC 3.2.1.22); further protease (EC 3.4), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); and/or beta-glucanase (EC 3.2.1.4 or EC 3.2.1.6).

In a particular embodiment these other enzymes are well-defined (as defined above for protease preparations).

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

Usually fat- and water-soluble vitamins, as well as trace minerals form part of a so-called premix intended for addition to the feed, whereas macro minerals are usually separately added to the feed. Either of these composition types, when enriched with a protease of the invention, is an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The following are non-exclusive lists of examples of these components:

Examples of fat-soluble vitamins are vitamin A, vitamin D3, vitamin E, and vitamin K, e.g. vitamin K3.

Examples of water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for piglet diets, and broiler diets, respectively).

TABLE 1

Typical vitamin recommendations

| Vitamin | Piglet diet | Broiler diet |
| --- | --- | --- |
| Vitamin A | 10,000-15,000 IU/kg feed | 8-12,500 IU/kg feed |
| Vitamin D3 | 1800-2000 IU/kg feed | 3000-5000 IU/kg feed |
| Vitamin E | 60-100 mg/kg feed | 150-240 mg/kg feed |
| Vitamin K3 | 2-4 mg/kg feed | 2-4 mg/kg feed |
| Vitamin B1 | 2-4 mg/kg feed | 2-3 mg/kg feed |
| Vitamin B2 | 6-10 mg/kg feed | 7-9 mg/kg feed |
| Vitamin B6 | 4-8 mg/kg feed | 3-6 mg/kg feed |
| Vitamin B12 | 0.03-0.05 mg/kg feed | 0.015-0.04 mg/kg feed |
| Niacin (Vitamin B3) | 30-50 mg/kg feed | 50-80 mg/kg feed |
| Pantothenic acid | 20-40 mg/kg feed | 10-18 mg/kg feed |
| Folic acid | 1-2 mg/kg feed | 1-2 mg/kg feed |
| Biotin | 0.15-0.4 mg/kg feed | 0.15-0.3 mg/kg feed |
| Choline chloride | 200-400 mg/kg feed | 300-600 mg/kg feed |

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

WO 01/58275 corresponds to U.S. Ser. No. 09/779,334 which is hereby incorporated by reference.

An animal feed composition according to the invention has a crude protein content of 50-800 g/kg, and furthermore comprises at least one protease as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Destillers Grains with Solubles (DDGS), typically in amounts of 0-30%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

Animal diets can e.g. be manufactured as mash feed (non pelleted) or pelleted feed. Typically, the milled feed-stuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) protease/enzyme preparation may also be added before or during the feed ingredient step. Typically a liquid protease/enzyme preparation is added after the pelleting step. The enzyme may also be incorporated in a feed additive or premix.

The final enzyme concentration in the diet is within the range of 0.01-200 mg enzyme protein per kg diet, for example in the range of 0.5-25 mg enzyme protein per kg animal diet.

The protease should of course be applied in an effective amount, i.e. in an amount adequate for improving hydrolysis, digestibility, and/or improving nutritional value of feed. It is at present contemplated that the enzyme is administered in one or more of the following amounts (dosage ranges): 0.01-200; 0.01-100; 0.5-100; 1-50; 5-100; 10-100; 0.05-50; or 0.10-10—all these ranges being in mg protease protein per kg feed (ppm).

For determining mg protease protein per kg feed, the protease is purified from the feed composition, and the specific activity of the purified protease is determined using a relevant assay (see under protease activity, substrates, and assays). The protease activity of the feed composition as such is also determined using the same assay, and on the basis of these two determinations, the dosage in mg protease protein per kg feed is calculated.

The same principles apply for determining mg protease protein in feed additives. Of course, if a sample is available of the protease used for preparing the feed additive or the feed, the specific activity is determined from this sample (no need to purify the protease from the feed composition or the additive).

Detergent Compositions

The protease of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the protease of the invention. The detergent additive as well as the detergent composition may comprise one or more other enzymes such as another protease, such as alkaline proteases from *Bacillus*, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258068 and EP 305216 or from *H. insolens* as described in WO 96/13580, a *Pseudomonas* lipase, e.g. from *P. alcaligenes* or *P. pseudoalcaligenes* (EP 218272), *P. cepacia* (EP 331376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422). Other examples are lipase variants such as those described in WO 92/05249, WO 94/01541, EP 407225, EP 260105, WO 95/35381, WO 96/00292, WO 95/30744, WO 94/25578, WO 95/14783, WO 95/22615, WO 97/04079 and WO 97/07202. Preferred commercially available lipase enzymes include Lipolase™ and Lipolase Ultra™ (Novozymes A/S). Suitable amylases (alpha- and/or beta-) include those of bacterial or fungal origin. Chemically modified or protein engineered mutants are included. Amylases include, for example, alpha-amylases obtained from *Bacillus*, e.g. a special strain of *B. licheniformis*, described in more detail in GB 1,296,839. Examples of useful amylases are the variants described in WO 94/02597, WO 94/18314, WO 95/26397, WO 96/23873, WO 97/43424, WO 00/60060, and WO 01/66712, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444. Commercially available amylases are Natalase™, Supramyl™, Stainzyme™, Duramy™, Termamyl™, Fungamyl™ and BAN™ (Novozymes A/S), Rapidase™ and Purastar™ (from Genencor International Inc.).

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259. Especially suitable cellulases are the alkaline or neutral cellulases having colour care benefits. Examples of such cellulases are cellulases described in EP 0 495257, EP 531372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and WO 99/01544. Commercially available cellulases include Celluzyme™, and Carezyme™ (Novozymes A/S), Clazinase™, and Puradax HA™ (Genencor International Inc.), and KAC-500(B)™ (Kao Corporation).

Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257. Commercially available peroxidases include Guardzyme™ (Novozymes).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per liter of wash liqour, preferably 0.05-5 mg of enzyme protein per liter of wash liqour, in particular 0.1-1 mg of enzyme protein per liter of wash liqour.

The enzyme of the invention may additionally be incorporated in the detergent formulations disclosed in WO 97/07202.

Nucleic Acid Constructs, Expression Vectors, Recombinant Host Cells, and Methods for Production of Proteases The present invention also relates to nucleic acid constructs, expression vectors and recombinant host cells comprising such polynucleotides encoding the proteases of the invention.

The present invention also relates to methods of producing a protease, comprising: (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides and fused polypeptides.

Preferably, the protein is a protease. For example, the protein may be a hydrolase, such as a proteolytic enzyme or protease.

The gene may be obtained from any prokaryotic, eukaryotic, or other source.

The present invention is further described by the following examples that should not be construed as limiting the scope of the invention.

EXAMPLES

Materials and Methods
Protease Assays
1) Suc-AAPR-pNA Assay:
pNA substrate: Suc-AAPR-pNA (Bachem L-1720).
Temperature: Room temperature (25° C.)
Assay buffers: 100 mM succinic acid, 100 mM HEPES, 100 mM CHES, 100 mM CABS, 1 mM $CaCl_2$, 150 mM KC, 0.01% Triton X-100 adjusted to pH-values 2.0, 3.0, 4.0, 5.0, 6.0, 7.0, 8.0, 9.0, 10.0, and 11.0 with HCl or NaOH.
20 µl protease (diluted in 0.01% Triton X-100) was mixed with 100 µl assay buffer. The assay was started by adding 100 µl pNA substrate (50 mg dissolved in 1.0 ml DMSO and further diluted 45× with 0.01% Triton X-100). The increase in $OD_{405}$ was monitored as a measure of the protease activity.

2) Suc-AAPF-pNA Assay:
pNA substrate: Suc-AAPF-pNA (Bachem L-1400).
Temperature: Room temperature (25° C.)
Assay buffers: 100 mM succinic acid, 100 mM HEPES, 100 mM CHES, 100 mM CABS, 1 mM $CaCl_2$, 150 mM KC, 0.01% Triton X-100, adjusted to pH-values 2.0, 3.0, 4.0, 5.0, 6.0, 7.0, 8.0, 9.0, 10.0, and 11.0 with HCl or NaOH.
20 µl protease (diluted in 0.01% Triton X-100) was mixed with 100 µl assay buffer. The assay was started by adding 100 µl pNA substrate (50 mg dissolved in 1.0 ml DMSO and further diluted 45× with 0.01% Triton X-100). The increase in $OD_{405}$ was monitored as a measure of the protease activity.

3) Protazyme OL Assay:
Substrate: Protazyme OL tablet (cross-linked and dyed collagen; from Megazyme)
Temperature: controlled (assay temperature).
Assay buffer: 100 mM succinic acid, 100 mM HEPES, 100 mM CHES, 100 mM CABS, 1 mM $CaCl_2$, 150 mM KC, 0.01% Triton X-100, adjusted to pH-values 2.0, 3.0, 4.0, 5.0, 6.0, 7.0, 8.0, 9.0, 10.0, and 11.0 with HCl or NaOH.

A Protazyme OL tablet was suspended in 2.0 ml 0.01% Triton X-100 by gentle stirring. 500 µl of this suspension and 500 µl assay buffer were dispensed in an Eppendorf tube and placed on ice. 20 µl protease sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm.). The incubation was stopped by transferring the tube back to the ice bath. Then the tube was centrifuged in an ice cold centrifuge for a few minutes and 200 µl supernatant was transferred to a microtiter plate. $OD_{650}$ was read as a measure of protease activity. A buffer blind was included in the assay (instead of enzyme).

4) Protazyme AK Assay:
Substrate: Protazyme AK tablet (cross-linked and dyed casein; from Megazyme)
Temperature: controlled (assay temperature).
Assay buffer: 100 mM succinic acid, 100 mM HEPES, 100 mM CHES, 100 mM CABS, 1 mM $CaCl_2$, 150 mM KC, 0.01% Triton X-100, pH 6.5.

A Protazyme AK tablet was suspended in 2.0 ml 0.01% Triton X-100 by gentle stirring. 500 µl of this suspension and 500 µl assay buffer were dispensed in an Eppendorf tube and placed on ice. 20 µl protease sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm.). The incubation was stopped by transferring the tube back to the ice bath. Then the tube was centrifuged in an ice cold centrifuge for a few minutes and 200 µl supernatant was transferred to a microtiter plate. $OD_{650}$ was read as a measure of protease activity. A buffer blind was included in the assay (instead of enzyme).

5) Suc-AAPX-pNA Assay:
pNA substrates: Suc-AAPA-pNA (Bachem L-1775)
  Suc-AAPR-pNA (Bachem L-1720)
  Suc-AAPD-pNA (Bachem L-1835)
  Suc-AAPI-pNA (Bachem L-1790)
  Suc-AAPM-pNA (Bachem L-1395)
  Suc-AAPV-pNA (Bachem L-1770)
  Suc-AAPL-pNA (Bachem L-1390)
  Suc-AAPE-pNA (Bachem L-1710)
  Suc-AAPK-pNA (Bachem L-1725)
  Suc-AAPF-pNA (Bachem L-1400)
Temperature: Room temperature (25° C.)
Assay buffer: 100 mM succinic acid, 100 mM HEPES, 100 mM CHES, 100 mM CABS, 1 mM $CaCl_2$, 150 mM KC, 0.01% Triton X-100, pH 4.0 or 9.0.

20 µl protease (diluted in 0.01% Triton X-100) was mixed with 100 µl assay buffer. The assay was started by adding 100 µl pNA substrate (50 mg dissolved in 1.0 ml DMSO and further diluted 45× with 0.01% Triton X-100). The increase in $OD_{405}$ was monitored as a measure of the protease activity.

Results are provided in Example 3 below.
Strains
Bacillus sp-19138 (19138) was isolated from a soil sample from Australia obtained in 1990 and provided to Novozymes A/S (former Novo Nordisk A/S).

Example 1: DNA-Preparation and Sequencing of the Bacillus Sp-19138 Genome

Chromosomal DNA of Bacillus sp-19138 (19138) was isolated by QIAamp DNA Blood Mini Kit (Qiagen, Hilden, Germany). 5 ug of chromosomal DNA of each strain were sent for genome sequencing at FASTERIS SA, Switzerland. The genome was sequenced by Illumina Sequencing. The genome sequence was analysed for secreted S53 proteases and the S53 protease (SEQ ID NO: 1/SEQ ID NO: 2) was identified.

Expression of Bacillus sp 19138 S53 Peptidase

A linear integration vector-system was used for the expression cloning of the S53 peptidase gene from Bacillus sp 19138 (SEQ ID NO: 1). The linear integration construct was a PCR fusion product made by fusion of the gene between two Bacillus subtilis homologous chromosomal regions along with a strong promoter and a chloramphenicol resistance marker. The fusion was made by SOE PCR (Horton, R. M., Hunt, H. D., Ho, S. N., Pullen, J. K. and Pease, L. R. (1989). Engineering hybrid genes without the use of restriction enzymes, gene splicing by overlap extension Gene 77: 61-68). The SOE PCR method is also described in patent application WO 2003095658. The gene was expressed under the control of a triple promoter system (as described in WO 99/43835), consisting of the promoters from Bacillus licheniformis alpha-amylase gene (amyL), Bacillus amyloliquefaciens alpha-amylase gene (amyQ), and the Bacillus thuringiensis cryIIIA promoter including stabilizing sequence. The gene coding for chloramphenicol acetyl-transferase was used as marker (described in e.g. Diderichsen, B.; Poulsen, G. B.; Joergensen, S. T.; A useful cloning vector for Bacillus subtilis. Plasmid 30:312 (1993)). The final gene constructs were integrated on the Bacillus chromosome by homologous recombination into the pectate lyase locus.

The gene fragment of the S53 gene was amplified from chromosomal DNA of the strain Bacillus sp. 19138 with gene specific primers containing overhang to the two flanking fragments. The upstream and downstream flanking fragments were amplified from genomic DNA of the strain iMB1361 (described in patent application WO 2003/095658). The S53 peptidase was expressed with a Bacillus lentus secretion signal (with the following amino acid sequence: MKKPLGKIVASTALLISVAFSSSIASA (amino acids −203−−177 of SEQ ID NO: 3) replacing the native secretion signal. It was expressed with a C-terminal HQHQHQH-tag (amino acids 436-442 of SEQ ID NO: 3) fused directly to the C-terminal. The expressed sequence is SEQ ID NO: 3.

The two vector fragments and the gene fragment was subjected to a Splicing by Overlap Extension (SOE) PCR reaction to assemble the three fragments into one linear vector construct. Two µl of the PCR product was transformed into Bacillus subtilis. Transformants were selected on LB plates supplemented with 6 µg of chloramphenicol per ml. A recombinant Bacillus subtilis clone containing the integrated expression construct was grown in liquid culture. The enzyme containing supernatant was harvested and the enzyme purified as described in Example 2.

Example 2: Purification of the S53 Protease from Bacillus Sp-19138

A Bacillus subtilis strain was constructed as indicated in Example 1 to express the S53 protease from Bacillus sp 19138 to the culture medium. The gene product is constructed to have a C-terminal -HQHQHQH tag (SEQ ID NO: 11) to facilitate its purification.

The culture broth was centrifuged (20000×g, 20 min) and the supernatant was carefully decanted from the precipitate. The supernatant was filtered through a Nalgene 0.2 µm filtration unit in order to remove the rest of the *Bacillus* host cells. The S53 protease was precipitated by addition of solid ammonium sulphate to the 0.2 μm filtrate to a final ammonium sulphate concentration of 3.2M (NH$_4$)$_2$SO$_4$ (80% saturation). After centrifugation (20000×g, 20 min) the precipitate was dissolved by addition of approx. 4 volumes of deionised water. The pH of the dissolved enzyme solution was adjusted to pH 7.5 with 3M Tris-base and applied to a Ni-NTA Superflow column (from QIAGEN) equilibrated in 50 mM HEPES/NaOH, 5 mM Imidazole, 500 mM NaCl, pH 7.5. After washing the column extensively with first the equilibration buffer and then with equilibration buffer with 15 mM imidazole, the protease was step-eluted with 50 mM HEPES/NaOH, 500 mM Imidazole, pH 7.5. Fractions were collected during elution and the S53 protease peak was transferred to 20 mM MES/NaOH, 1 mM CaCl$_2$, pH 6.5 on a G25 Sephadex column (from GE Healthcare). The pH of the G25 sephadex transferred enzyme was adjusted to pH 7.5 with 3M Tris-base and the solutions was applied to a Q-sepharose FF column (from GE Healthcare) equilibrated in 20 mM HEPES/NaOH, 1 mM CaCl$_2$, pH 7.5. After washing the column extensively with the equilibration buffer, the protease was eluted with a linear NaCl gradient (0→0.5M) in the same buffer over eight column volumes. Fractions from the column were analysed for protease activity (using the Protazyme OL assay at pH 4) and active fractions were further analysed by SDS-PAGE. Pure fractions were pooled and the pH in the pool was adjusted to pH 6.0 with 20% CH$_3$COOH. The pH adjusted pool was the purified preparation and was used for further characterization.

Example 3: Characterization of the S53 Protease from *Bacillus* Sp 19138

The Suc-AAPR-pNA assay was used for obtaining the pH-activity profile. The Protazyme OL assay was used for obtaining the pH-stability profile (residual activity after 2 hours at indicated pH-values). For the pH-stability profile, the protease was diluted 7× in the different pH 2 to pH 11 assay buffers to reach the pH-values of these buffers and then incubated for 2 hours at 37° C. After incubation, the pH of the protease incubations was returned to the same pH-value of the sample before the assay for residual activity, by diluting the sample with pH 4.0 assay buffer. The Protazyme OL assay was used for obtaining the temperature-activity profile at pH 4.0. The Suc-AAPX-pNA assay and ten different Suc-AAPX-pNA substrates were used for obtaining the P1-specificity of the S53 protease at pH 4.0. Data for Protease 10R was obtained using slightly different conditions. The pH-activity profile was on Suc-AAPF-pNA, the pH-stability profile used Suc-AAPF-pNA as activity substrate, the temperature profile was on Protazyme AK at pH 6.5 and the P1-specificity profile was at pH 9.0.

The results are shown in Tables 2-5 below. For Table 2, the activities are relative to the optimal pH for the enzyme. For Table 3, the activities are residual activities relative to a sample, which was kept at stable conditions (5° C., pH 4.0 or pH 9.0). For Table 4, the activities are relative to the optimal temperature at pH 4.0 (pH 6.5 for Protease 10R) for the enzyme. For Table 5, the activities are relative to the best substrate for the enzyme.

TABLE 2 pH-activity profile

| pH | S53 protease from *Bacillus* sp 19138 | Protease 10R |
|---|---|---|
| 2 | 0.01 | — |
| 3 | 0.16 | 0.00 |
| 4 | 0.86 | 0.02 |
| 5 | 1.00 | 0.07 |
| 6 | 0.14 | 0.21 |
| 7 | 0.01 | 0.44 |
| 8 | 0.00 | 0.67 |
| 9 | 0.00 | 0.88 |
| 10 | 0.00 | 1.00 |
| 11 | 0.00 | 0.93 |

TABLE 3 pH-stability profile (residual activity after 2 hours at 37° C.)

| pH | S53 protease from *Bacillus* sp 19138 | Protease 10R |
|---|---|---|
| 2 | 0.00 | 0.78 |
| 3 | 0.83 | 1.03 |
| 4 | 1.16 | 0.99 |
| 5 | 1.11 | 1.00 |
| 6 | 1.14 | 1.03 |
| 7 | 0.94 | 1.01 |
| 8 | 0.03 | 0.98 |
| 9 | 0.03 | 0.99 |
| 10 | 0.05 | 0.99 |
| 11 | 0.07 | 0.86 |
| After 2 hours at 5° C. | 1.00 (at pH 4) | 1.00 (at pH 9) |

TABLE 4

Temperature activity profile at pH 4.0 or pH 6.5

| Temp (° C.) | S53 protease from *Bacillus* sp 19138 (pH 4) | Protease 10R (pH 6.5) |
|---|---|---|
| 15 | 0.08 | 0.01 |
| 25 | 0.32 | 0.02 |
| 37 | 0.59 | 0.06 |
| 50 | 0.91 | 0.13 |
| 60 | 1.00 | 0.35 |
| 70 | 0.43 | 0.96 |
| 80 | 0.17 | 1.00 |
| 90 | — | 0.18 |

TABLE 5

P1-specificity on 10 Suc-AAPX-pNA substrates at pH 4.0 or pH 9.0

| Suc-AAPX-pNA | S53 protease from *Bacillus* sp 19138 (pH 4) | Protease 10R (pH 9) |
|---|---|---|
| Suc-AAPA-pNA | 0.07 | 0.13 |
| Suc-AAPR-pNA | 1.00 | 0.09 |
| Suc-AAPD-pNA | 0.00 | 0.00 |
| Suc-AAPI-pNA | 0.00 | 0.00 |
| Suc-AAPM-pNA | 0.08 | 0.78 |
| Suc-AAPV-pNA | 0.00 | 0.01 |
| Suc-AAPL-pNA | 0.06 | 0.18 |
| Suc-AAPE-pNA | 0.01 | 0.00 |
| Suc-AAPK-pNA | 0.12 | 0.08 |
| Suc-AAPF-pNA | 0.01 | 1.00 |

The pH-activity on the Suc-AAPR-pNA substrate, the pH-stability profile (residual activity after 2 hours at 37° C.), the temperature activity profile on Protazyme OL at pH 4.0 and the P1-specificity on 10 Suc-AAPF-pNA substrates at pH 4.0 for the S53 protease from *Bacillus* sp 19138 are also shown in FIGS. 2-5 compared with the data for Protease 10R.

Other Characteristics for the S53 Protease from *Bacillus* Sp 19138

Determination of the N-terminal sequence was: VTPNPTG (amino acids 1-7 of SEQ ID NO: 6).

The relative molecular weight as determined by SDS-PAGE was approx. $M_r$=52 kDa.

The molecular weight determined by intact molecular weight analysis was 46811.5 Da.

The mature sequence (from MS data, EDMAN data, *Bacillus* sp 19138 translated sequence plus five of the seven amino acid residues of the HQ-tag (HQHQH) (amino acids 436-440 of SEQ ID NO: 6) gives):

(SEQ ID NO: 6)
VTPNPTGRMTNDLVSRYNVQPLYTKGANGSGQTIGIVTLADFNPSDAYS

YWQYNNINVNPNRITKINVDGGSGLSEDAGSDETSLDVEQSGALAPGAN

LNVYVGPNTDTGFVDAYAKAINDNVAHQISASWGESESLINYYVQQQME

TPEYAETFNQLFMQAAAQGTSMFASAGDSGAYDASGDLNTYDLSVDNPA

DSPYITAAGGTTVPFTYTSTQYNLSITVPQERAWGWDYLYPLFDARGLN

NPTGWAQRYFVGGGGGFSQLFATPDYQTGVSGVNSYTAVHQWTPSSDFT

SVTRDAQPTIVTGTGTGRNLPDLSMNADPYTGYSVYFNLPTTNGATTVD

SGWATYGGTSFVAPQLAGLSALINSANGSEAGFWNPQLYRFAQSNHSPL

HPLNTAGASNDNVFYSGTPGAIYNQATGLGTPDVTALAQAFGKHQHQH

The calculated molecular weight from this mature sequence was 46810.2 Da.

These data suggests that two amino acid residues (QH) of the -HQHQHQH tag (amino acids 436-442 of SEQ ID NO: 3) are cleaved from the C-terminal of the gene product, possibly due to auto proteolysis.

Example 4: Soybean-Maize Meal Activity Assay

An end-point assay using soybean-maize meal as substrate was used for obtaining the activity profile of the proteases at pH 3-7.

Assay buffers: 100 mM succinic acid, 100 mM HEPES, 100 mM CHES, 100 mM CAPS, 1 mM CaCl2, 150 mM KC, 0.01% Triton X-100 were prepared and adjusted using HCl or NaOH to a pH value such that after soybean-maize meal substrate (1 g, 30:70 ratio) had been mixed with assay buffer (10 mL) to give a slurry, the final pH of the slurry was one of the following pH's: 3.0, 4.0, 5.0, 6.0 and 7.0.

2 mL soybean-maize meal slurry was mixed for 30 min before protease addition and incubation for 3 hours at 40° C. (500 rpm). Protease was added via 100 μl 100 mM sodium acetate buffer (9.565 g/L NaOAc, 1.75 g/L acetic acid, 5 mM $CaCl_2$, 0.01% BSA, 0.01% Tween20, pH 6.0). Supernatants were collected after centrifugation (10 min, 3000×g, 0° C.) and protease activity was determined using a colorimetric assay based on the o-phthal-dialdehyde (OPA) method essentially according to Nielsen et al. (Nielsen, P M, Petersen, D, Dampmann, C. Improved method for determining food protein degree of hydrolysis. J Food Sci, 2001, 66: 642-646). This assay detects free α-amino groups and hence protease activity can be measured as an increase in absorbance. First 500 μl of each supernatant was filtered through a 100 kDa Microcon filter by centrifugation (60 min, 12,000×g, 5° C.). The samples were diluted 10× in deionized water and 25 μl of each sample was loaded into a 96 well microtiter plate (5 replicates). Finally 200 μl OPA reagent was dispensed into all wells and the plate was shaken (10 sec, 750 rpm) and absorbance measured at 340 nm. The level of protease activity was calculated as the difference between absorbance in the enzyme treated sample and the blank sample and expressed as 'OD×dilution factor'.

Figure 5:
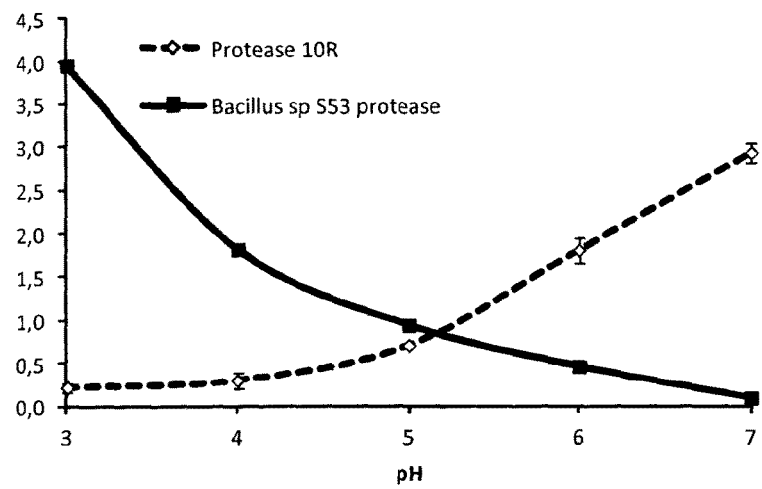

The results are shown in FIG. 5 and table 6 below. The proteolytic activity of the S53 protease from *Bacillus* sp 19138 on soybean-maize meal was high at pH 3 and decreased with increasing pH. At pH 3 and 4 the activity was significantly higher than for protease 10R indicating that the S53 protease from *Bacillus* sp 19138 could be a much more efficient enzyme in the upper gut of monogastrics where there is an acidic pH environment.

TABLE 6

Protease activity on soybean-maize meal at pH 3.0, 4.0, 5.0, 6.0 and 7.0

| | S53 protease from *Bacillus* sp 19138 | | Protease 10R | |
|---|---|---|---|---|
| pH | Average | Standard deviation | Average | Standard deviation |
| 3.0 | 3.95 | 0.08 | 0.22 | 0.06 |
| 4.0 | 1.82 | 0.03 | 0.30 | 0.10 |
| 5.0 | 0.94 | 0.02 | 0.71 | 0.01 |
| 6.0 | 0.46 | 0.01 | 1.81 | 0.14 |
| 7.0 | 0.09 | 0.02 | 2.92 | 0.11 |

Example 5: Protein Degrading Activity Under Gizzard Conditions

Gizzard digesta material from 21 day old broiler chickens fed a corn-soy diet was collected; freeze dried and ground using a small coffee mill. The ground gizzard sample was suspended (47% w/v) in buffer (100 mM succinic acid, 1 mM $CaCl_2.2H_2O$, 150 mM KC, 0.01% Triton X-100, adjusted to pH 3 using HCl) and left at 4° C. over night. The suspension was heated to 40° C. and 1 ml was dispensed into tubes kept at 40° C. Three tubes representing blank (0 h) were immediately centrifuged (3000×g, 0° C., 10 min) and supernatants frozen. Enzyme was added to the remaining tubes via 50 μL 100 mM sodium acetate buffer (9.565 g/l NaOAc, 1.75 g/L acetic acid, 5 mM $CaCl_2$, 0.01% BSA, 0.01% Tween20, pH 6.0) and the samples were incubated for 1 hour at 40° C. while shaking (500 rpm). The samples were centrifuged (3000×g, 0° C., 10 min) and supernatants recovered and frozen. The protein hydrolyzing effect of the protease was determined by analyzing free α-amino groups in the supernatants using the assay described under 'soybean-maize meal activity assay'.

Figure 6:
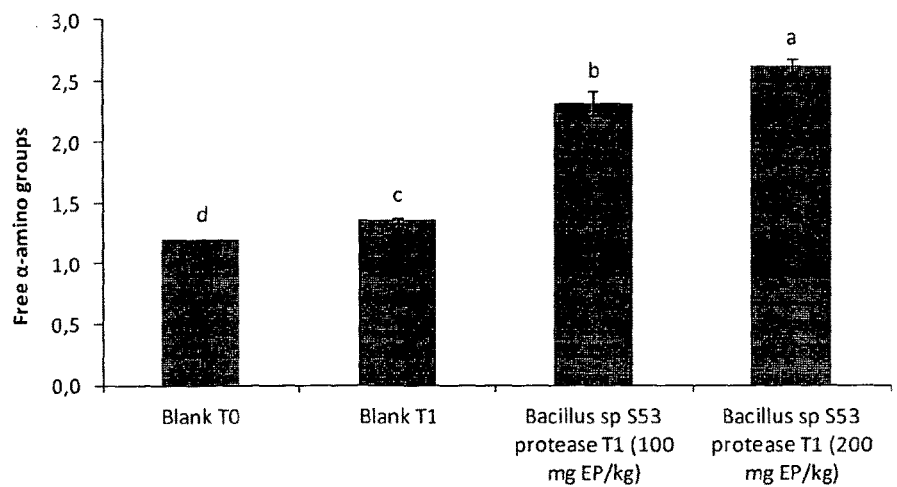
FIG. 6 shows the level of free α-amino groups after incubation of gizzard digesta for 1 hour at increasing protease dose compared to a sample that was not incubated.

The results (FIG. 6 and table 7) showed a significant increase in free α-amino groups in blank samples incubated for 1 hour compared to blank samples not allowed to incubate. This indicates that there is active protease in the digesta samples most likely from pepsin, which is present in the gizzard of broilers. Upon inclusion of the S53 protease from *Bacillus* sp 19138, the level of free α-amino groups was further increased in a dose-response manner. These data suggest that the S53 protease from *Bacillus* sp 19138 will be able to degrade protein in the gizzard of broilers and act on top of the pepsin activity already present in the gizzard.

TABLE 7

Free α-amino groups after incubation of gizzard digesta at pH 3 with increasing dose of S53 protease from *Bacillus* sp 19138 (1 h, 40° C.) compared to a sample that was not incubated

| Treatment (incubation time, hours; pH 3) | Enzyme dose (mg/kg dm) | Number of repetitions, n | Free α-amino groups (mean ± STD) |
|---|---|---|---|
| Blank (0 h) | 0 | 3 | 1.20 ± 0.01 [d] |
| Blank (1 h) | 0 | 3 | 1.36 ± 0.02 [c] |
| *Bacillus* sp S53 protease (1 h) | 100 | 3 | 2.31 ± 0.10 [b] |
| *Bacillus* sp S53 protease (1 h) | 200 | 3 | 2.62 ± 0.06 [a] |

[a, b, c, d] Different superscript letters indicate statistical differences. Comparison of means was done using the Tukey test (α = 0.05) provided by the ANOVA procedure (SAS Institute Inc.).

Example 6: In Vitro Digestion Assay Simulating Gastric and Small Intestinal Digestion An in vitro digestion assay was used to evaluate the effect of the proteases on a feed substrate (soybean-maize meal) in a setup designed to simulate gastric and small intestinal digestion in monogastric animals.

The incubation process consisted of a gastric digestion phase with porcine pepsin (SP7000, Sigma-Aldrich, St. Louis, Mo., USA) at pH 3 followed by a short duodenal incubation at pH 3.8 and a small intestinal incubation with pancreatin (8×USB, P-7545, Sigma-Aldrich, St. Louis, Mo., USA) at pH 7.0.

The in vitro digestion was performed using an automated system based on a Gilson liquid handler (Biolab, Denmark). For each sample 0.8 g feed was weighed into a tube and all tubes were placed in the liquid handler (40° C., 500 rpm). Additions of solutions as well as pH measurements were performed automatically. At time 0 min, 4.1 mL HCl (24 mM $CaCl_2$) was added to reach pH 3.0 in the solution. At time 30 min 0.5 ml HCl (24 mM $CaCl_2$, 3000 U pepsin/g feed) and 100 μL of a 100 mM sodium acetate buffer (258.6 g NaOAc per liter, 0.57% acetic acid, pH 6.0) was added. At time 90 min 900 μL NaOH was added to reach pH~3.8 and at time 120 min 400 μL of a 1 M $NaHCO_3$ solution containing 6.5 mg pancreatin/g feed was added leading to pH 6.8 in the solution. The pH was measured at time 30, 60, 90, 115, 120 and 180 min. The test proteases were added via the 100 μL NaOAc buffer at time 30 min.

The degree of protein hydrolysis (DH) was determined using a colorimetric assay based on the o-phthal-dialdehyde (OPA) method essentially according to Nielsen et al. (Nielsen, P M, Petersen, D, Dampmann, C. Improved method for determining food protein degree of hydrolysis. J Food Sci, 2001, 66: 642-646). This assay detects free α-amino groups and hence protease activity can be measured as an increase in absorbance. First 500 μL of each supernatant is filtered through a 100 kDa Microcon filter by centrifugation (60 min, 11,000 rpm, 5° C.). The samples are diluted 100× in deionized water and 25 μL of each sample is loaded into a 96 well microtiter plate (5 replicates). Finally 200 μL OPA reagent is dispensed into all wells and the plate is shaken (10 sec, 750 rpm) and absorbance measured at 340 nm. The percentage of cleaved peptide bonds (DH) was calculated as:

$$DH(\%) = 100 \times h/h_{tot}$$

where $h_{tot}$ is the total number of peptide bonds per protein equivalent, and h is the number of hydrolyzed bonds. Calculation of $h_{tot}$ is based on the amino acid sequence of the raw material. In this study the value for soy was used (7.8 g equivalents per kg protein) according to Adler-Nissen (J. Enzymic Hydrolysis of Food Proteins. Elsevier Applied Science Publishers. 1986). The expression for h in the OPA method is:

$$h = (\text{serine-NH}_2 - \beta)/\alpha \text{ megv/g protein},$$

where α=0.970 and β=0.342 according to Adler-Nissen (Determination of the degree of hydrolysis of food protein hydrolysates by trinitrobenzenesulfonic acid. Journal of Agricultural and Food Chemistry, 27: 1256-1262. 1979). Serine-$NH_2$ is calculated as:

$$\text{Serine-NH}_2 = (OD_{blank} - OD_{sample})/(OD_{standard} - OD_{blank}) \times 0.9516 \text{ meqv/L} \times 0.1 \times 100/X \times P,$$

where serine-$NH_2$=meqv serine-$NH_2$/g protein; X=g sample; P=protein % in sample and 0.1 is the sample volume in liters (L).

Statistics: Statistical analysis of the parameters registered was performed using an analysis of variance (ANOVA) procedure and comparison of means was done using the Student t-test (α=0.05) provided by the ANOVA procedure (SAS, JMP® 5 Administrators Guide to Annually Licensed Windows, Mackintosh, and Linux Versions, Release 5.1. SAS Institute, Cary, N.C. (2003)).

The results (Table 8 and FIG. 7) showed that while the 10R protease did not have an effect on the degree of protein hydrolysis (DH) during the gastric incubation of the in vitro digestion, the S53 protease from *Bacillus* sp 19138 significantly increased DH. After the full in vitro digestion procedure including both gastric and intestinal incubation, the 10R protease had significantly increased DH whereas the effect by the S53 protease from *Bacillus* sp 19138 was only numerical. The activity of the S53 protease from *Bacillus* sp 19138 during the gastric incubation presents a new opportunity to obtain protein hydrolysis early in the digestion process and might also present an opportunity to obtain an increased protein digestibility by mixing proteases acting in the gastric and intestinal compartments respectively.

TABLE 8

Degree of hydrolysis (DH, %) in in vitro digestion samples after treatment with S53 protease from *Bacillus* sp 19138 or Protease 10R and measured after the gastric incubation and the full gastric + intestinal incubation

| Treatment | Number of repetitions, N | DH (%) measured after gastric incubation | | DH (%) measured after full incubation | |
|---|---|---|---|---|---|
| | | Average | Std. | Average | Std. |
| Control | 5 | 2.50 [b] | 0.09 | 29.65 [b] | 1.25 |
| S53 protease from *Bacillus* sp 19138 S53 protease | 5 | 5.04 [a] | 0.23 | 30.20 [b] | 0.31 |
| Protease 10R | 5 | 2.49 [b] | 0.09 | 33.22 [a] | 1.20 |

[a, b] Different superscript letters within each column indicate statistical differences.

Figure 7:
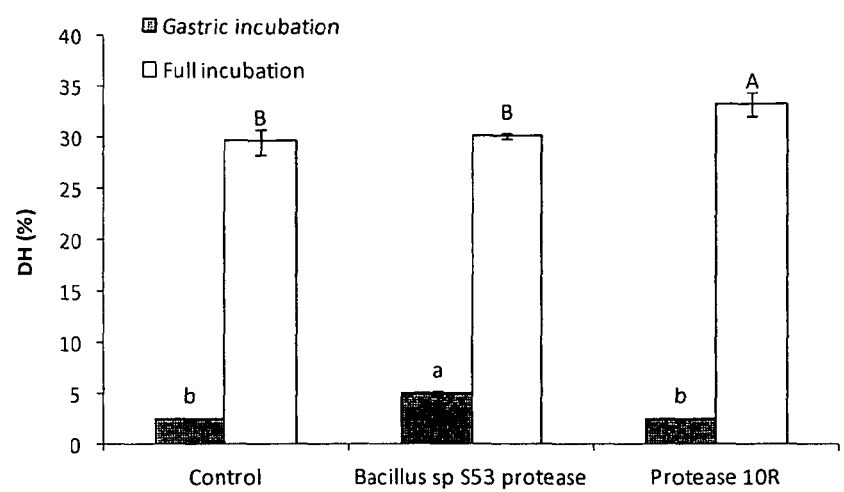
FIG. 7 shows the degree of protein hydrolysis (DH, %) in in vitro digestion samples after treatment with the S53 protease from *Bacillus* sp 19138 or Protease 10R and measured after the gastric incubation (■) and the full gastric+intestinal incubation (□). Different letters indicate statistically significant differences.

FIG. 7 shows the degree of hydrolysis (DH, %) in in vitro digestion samples after treatment with S53 protease from *Bacillus* sp 19138 or Protease 10R and measured after the gastric incubation and the full gastric+intestinal incubation. Different letters indicate statistical significant differences.

Example 7: Proteolytic Activity on Crop, Gizzard and Ileum Digesta

Crop, gizzard and ileum digesta material from 21 day old broiler chickens fed a corn-soy diet was collected; freeze dried and ground using a small coffee mill. The ground samples were suspended (47% w/v) in the following buffers and left to hydrate at 4° C. over night (no stirring):

Crop buffer: 100 mM HEPES, 1 mM $CaCl_2.2H_2O$, 150 mM KC, 0.01% Triton X-100, adjusted to pH 5 using HCl Gizzard buffer: 100 mM succinic acid, 1 mM $CaCl_2.2H_2O$, 150 mM KC, 0.01% Triton X-100, adjusted to pH 1.67 using HCl Ileum buffer: 100 mM HEPES, 1 mM $CaCl_2.2H_2O$, 150 mM KC, 0.01% Triton X-100, adjusted to pH 7.2 using HCl The resulting pH was: pH 5 in crop samples; pH 3 in gizzard samples; and pH 7 in ileum samples. The suspensions were heated to 40° C. and 1 mL was dispensed into tubes kept at 40° C. Three tubes representing blank ($T_0$) were immediately centrifuged (3000×g, 0° C., 10 min) and supernatants frozen. Enzyme (200 mg enzyme protein/kg substrate) was added to the remaining tubes via 50 μL 100 mM sodium acetate buffer (9.565 g/l NaAc, 1.75 g/l acetic acid, 5 mM $CaCl_2$, 0.01% BSA, 0.01% Tween20, pH 6.0) and the crop and ileum samples were incubated for 3 hours ($T_3$) while the gizzard samples were incubated for 1 hour ($T_1$) at 40° C. while shaking (500 rpm). The samples were centrifuged (3000×g, 0° C., 10 min) and supernatants recovered and frozen. The proteolytic activity was determined by analyzing primary amines using the o-phthaldialdehyde (OPA) assay.

The results are shown in Table 9. For each of the digesta types (crop, gizzard and ileum) there was a significant difference between the level of primary amines in the blank $T_0$ sample and the blank samples incubated for 1 or 3 hours. This difference can be ascribed to activity of proteases present in the substrate and originating from either the diet raw materials or the animal. During incubation of the crop and gizzard digesta the S53 protease from Bacillus sp 19138 further increased the level of primary amines compared to the blank sample incubated for 3 hours (crop) or 1 hour (gizzard), demonstrating that the protease had a proteolytic activity on this substrate under the given conditions. It was not possible to distinguish between the activity of the S53 protease from Bacillus sp and Protease 10R under crop or ileum conditions, whereas under gizzard conditions the S53 protease from Bacillus sp 19138 performed significantly better than Protease 10R. Both proteases numerically increased the level of primary amines under ileum conditions. These data indicate that the S53 protease from Bacillus sp 19138 has the potential to degrade feed protein along the entire gastrointestinal tract of poultry and swine but in particular in the upper gastrointestinal tract, where pH tends to be slightly more acidic than in other parts.

TABLE 9

Proteolytic activity of the S53 protease from Bacillus sp 19138 compared to Protease 10R when incubated with broiler digesta and expressed as level of primary amines measured by the OPA assay ($OD_{340}$ × dilution factor)

| Treatment | Crop (3 hours) | Gizzard (1 hour) | Ileum (3 hours) |
|---|---|---|---|
| Blank ($T_0$) | 1.78 ± 0.01$^d$ | 3.15 ± 0.01$^d$ | 8.55 ± 0.23$^b$ |
| Blank | 2.86 ± 0.11$^c$ | 3.96 ± 0.09$^{bc}$ | 13.94 ± 0.23$^a$ |
| Protease 10R | 3.21 ± 0.05$^{ab}$ | 3.99 ± 0.06$^b$ | 14.32 ± 0.18$^a$ |
| S53 protease from Bacillus sp 19138 | 3.25 ± 0.03$^{ab}$ | 4.30 ± 0.02$^a$ | 14.13 ± 0.23$^a$ |

$^{a,b,c,d}$Values within a column that are not connected by the same superscript letters are statistically different as determined by the Tukey Kramer test (α = 0.05) provided by the ANOVA procedure (SAS Institute Inc.).

Example 8: Thermostability

An aliquot of the protein sample of protease (purified as described in Example 2) is either desalted or buffer-changed into 20 mM Na-acetate, pH 4.0 using a prepacked PD-10 column or dialysed against 2×500 ml 20 mM Na-acetate, pH 4.0 at 4° C. in a 2-3 h step followed by an overnight step. The sample is 0.45 μm filtered and diluted with buffer to approx. 2 A280 units. The dialysis buffer is used as reference in Differential Scanning calorimetry (DSC). The samples are degassed using vacuum suction and stirring for approx. 10 minutes.

A DSC scan is performed on a MicroCal VP-DSC at a constant scan rate of 1.5° C./min from 20-90° C. Data-handling is performed using the MicroCal Origin software (version 4.10), and the denaturation temperature, $T_d$ (also called the melting temperature, $T_m$) is defined as the temperature at the apex of the peak in the thermogram.

Example 9: Steam Stability

Residual activity of the protease after steam treatment may be evaluated using the following assay.

In these experiments a modified set-up is used whereby the steam is provided from a steam generator and led into the box. The samples placed on a plate are inserted into the box through a drawer when the temperature has reached ca. 93-94° C. Upon the insertion of the samples the temperature drops 4° C. Incubation is performed for 30 seconds while the temperature remains approximately constant at 90° C. Thereafter the plate is quickly removed from the box, the samples placed on ice, re-suspended and evaluated with respect to protease activity using the Suc-AAPF-pNA or o-Phthaldialdehyde (OPA) assay. Each enzyme sample is compared to a similar sample that had not been steam treated in order to calculate residual activity.

Example 10: Pelleting Stability Tests

The enzyme granulation is performed in a manner as described in U.S. Pat. No. 4,106,991, Example 1. The obtained granulate is dried in a fluid bed to a water content below 1% and sifted to obtain a product with the particle range 250 μm to 850 μm. Finally, the product is coated with palm oil and calcium carbonate in a manner as described in U.S. Pat. No. 4,106,991, Example 22.

Approximately 50 g enzyme granulate is pre-mixed with 10 kg feed for 10 minutes in a small horizontal mixer. This premix is mixed with 90 kg feed for 10 minutes in a larger horizontal mixer. From the mixer the feed is led to the conditioner (a cascade mixer with steam injection) at a rate of approximately 300 kg/hour. The conditioner heats up the feed to 95° C. (measured at the outlet) by injecting steam.

The residence time in the conditioner is 30 seconds. From the conditioner the feed is led to a Simon Heesen press equipped with 3.0×35 mm horizontal die and pressed to pellets with a length of around 15 mm. After the press the pellets are placed in an air cooler and cooled for 15 minutes.

The protease activity is measured using the Suc-AAPF-pNA assay prior to pelleting and in the feed pellets after pelleting. Pelleting stability is determined by comparing the protease activity in pelleted feed relative to the activity in non-pelleted feed.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

---

What is claimed is:

1. A method for improving the nutritional value of an animal feed, comprising adding at least one polypeptide having protease activity to the feed, wherein the amino acid sequence of the polypeptide has at least 95% sequence identity to the polypeptide of SEQ ID NO: 5.

2. A method for the treatment of proteins, comprising adding at least one polypeptide having protease activity to at least one protein or protein source, wherein the amino acid sequence of the polypeptide has at least 95% sequence identity to the polypeptide of SEQ ID NO: 5.

3. The method of claim 2, wherein the protein source comprises soybean.

4. The method of claim 1, wherein the amino acid sequence of the polypeptide has at least 97% sequence identity to the polypeptide of SEQ ID NO: 5.

5. The method of claim 1, wherein the amino acid sequence of the polypeptide has at least 99% sequence identity to the polypeptide of SEQ ID NO: 5.

6. The method of claim 1, wherein the polypeptide is encoded by a polynucleotide that hybridizes under high stringency conditions with
   (i) the mature polypeptide coding sequence of SEQ ID NO: 1, or
   (ii) the full-length complementary strand of (i) or (ii);
wherein the high stringency conditions are defined as pre-hybridization and hybridization at 42° C. in 5×SSPE, 0.3% SDS, 200 micrograms/ml sheared and denatured salmon sperm DNA, and 50% formamide, following standard Southern blotting procedures for 12 to 24 hours, followed by washing three times each for 15 minutes using 2×SSC, 0.2% SDS at 65° C.

7. The method of claim 1, wherein the polypeptide is a variant of the polypeptide of SEQ ID NO: 5 comprising a substitution, deletion, and/or insertion of one or more amino acids.

8. The method of claim 1, wherein the polypeptide is a fragment of the polypeptide of SEQ ID NO: 5.

9. The method of claim 1, wherein the polypeptide has the amino acid sequence of SEQ ID NO: 5.

10. A recombinant host cell comprising a polynucleotide encoding a polypeptide having protease activity, wherein the polynucleotide is operably linked to one or more control sequences that direct the production of the polypeptide in the recombinant host cell and wherein the polypeptide has at least 95% sequence identity to the polypeptide of SEQ ID NO: 5.

11. A method of producing a polypeptide having protease activity, comprising:
   (a) cultivating the host cell of claim 10 under conditions conducive for production of the polypeptide; and
   (b) recovering the polypeptide.

12. The method of claim 11, wherein the amino acid sequence of the polypeptide has at least 97% sequence identity to the polypeptide of SEQ ID NO: 5.

13. The method of claim 11, wherein the amino acid sequence of the polypeptide has at least 99% sequence identity to the polypeptide of SEQ ID NO: 5.

14. The method of claim 11, wherein the polypeptide is encoded by a polynucleotide that hybridizes under high stringency conditions with
   (i) the mature polypeptide coding sequence of SEQ ID NO: 1, or
   (ii) the full-length complementary strand of (i) or (ii);
wherein the high stringency conditions are defined as pre-hybridization and hybridization at 42° C. in 5×SSPE, 0.3% SDS, 200 micrograms/ml sheared and denatured salmon sperm DNA, and 50% formamide, following standard Southern blotting procedures for 12 to 24 hours, followed by washing three times each for 15 minutes using 2×SSC, 0.2% SDS at 65° C.

15. The method of claim 11, wherein the polypeptide is a variant of the polypeptide of SEQ ID NO: 5 comprising a substitution, deletion, and/or insertion of one or more amino acids.

16. The method of claim 11, wherein the polypeptide is a fragment of the polypeptide of SEQ ID NO: 5.

17. The method of claim 11, wherein the polypeptide has the amino acid sequence of SEQ ID NO: 5.

* * * * *